(12) United States Patent
DiCicco et al.

(10) Patent No.: US 11,685,913 B1
(45) Date of Patent: *Jun. 27, 2023

(54) T4 DNA LIGASE VARIANTS WITH INCREASED RESISTANCE TO SALT

(71) Applicant: AbClonal Science, Inc., Woburn, MA (US)

(72) Inventors: Alicia DiCicco, Salem, MA (US); Zhenyu Zhu, Lynnfield, MA (US); Aine Quimby, Newburyport, MA (US)

(73) Assignee: AbClonal Science, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/675,278

(22) Filed: Feb. 18, 2022

(51) Int. Cl.
 *C12N 9/00* (2006.01)
 *C12Q 1/6869* (2018.01)

(52) U.S. Cl.
 CPC ............. *C12N 9/93* (2013.01); *C12Q 1/6869* (2013.01); *C12Y 605/01001* (2013.01)

(58) Field of Classification Search
 None
 See application file for complete search history.

(56) References Cited

U.S. PATENT DOCUMENTS 10,837,009 B1   11/2020   Ong

OTHER PUBLICATIONS

Ngo et al. in the Protein Folding Problem and Tertiary Structure Prediction, 1994, Merz et al. (ed.), Birkhauser, Boston, MA, pp. 433 and 492-495.*

* cited by examiner

*Primary Examiner* — Richard G Hutson
(74) *Attorney, Agent, or Firm* — Eric P. Mirabel, JD, LLM

(57) ABSTRACT

A number of T4 DNA ligase mutants exhibiting enhanced ligation activity in the presence of high salt concentrations compared to the wild-type ligase were engineered, characterized, and selected via gel electrophoresis of ligation products from a standard ligation assay. Ligase catalyzes the formation of phosphodiester bonds between the 5' and 3' ends of complementary cohesive ends or blunt ends of duplex DNA, a process that is vital to numerous molecular biology processes including cloning and sequencing.

9 Claims, 3 Drawing Sheets

Specification includes a Sequence Listing.

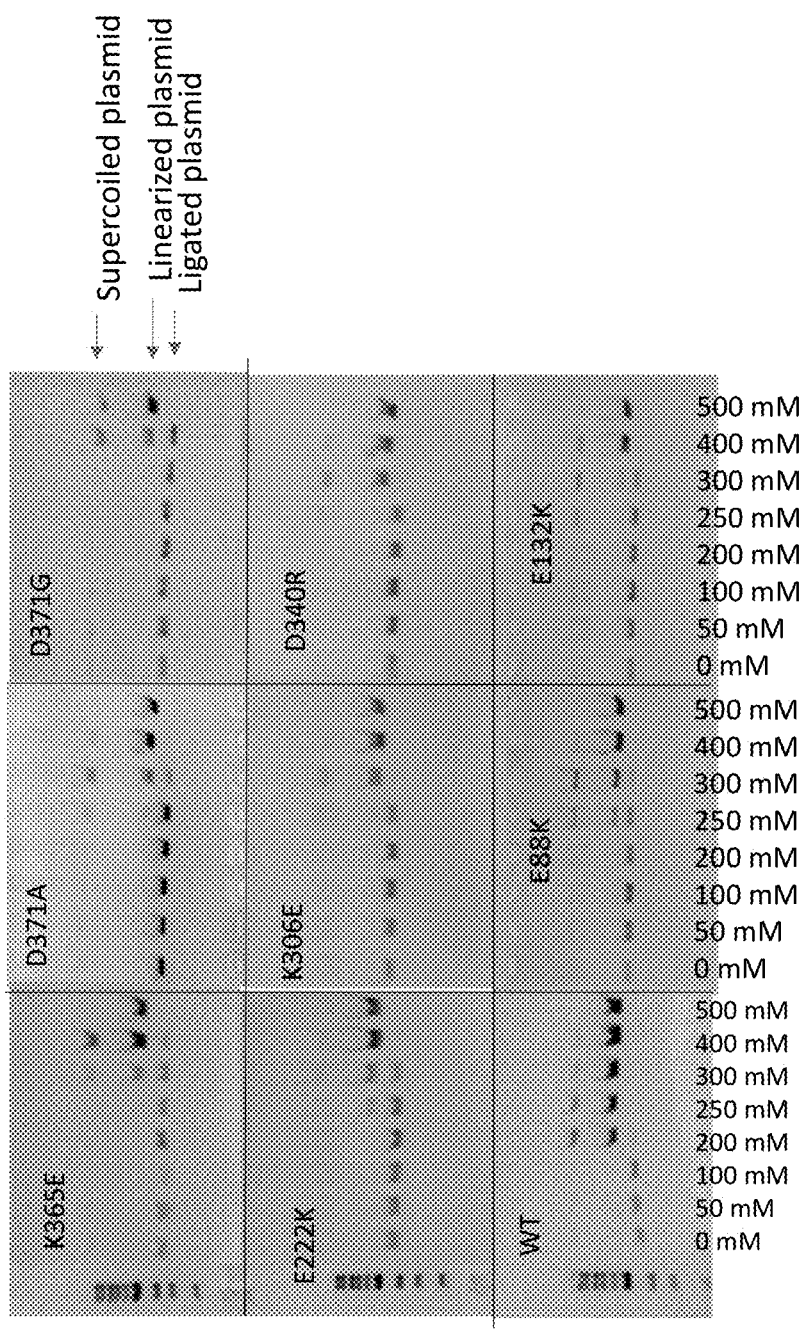
Figure 1A: T4 DNA Ligase Variants in Increasing NaCl Concentrations (composite gel image)

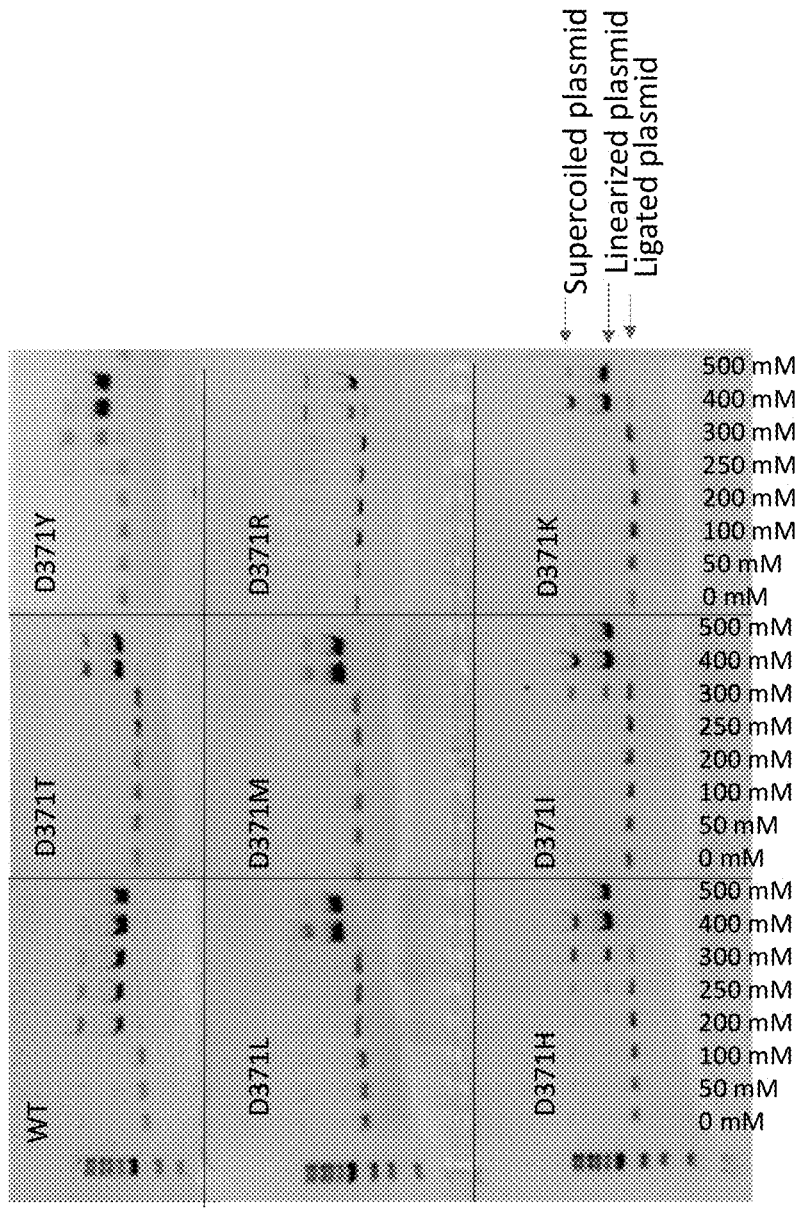
Figure 1B: T4 DNA Ligase Variants in Increasing NaCl Concentrations (composite gel image)

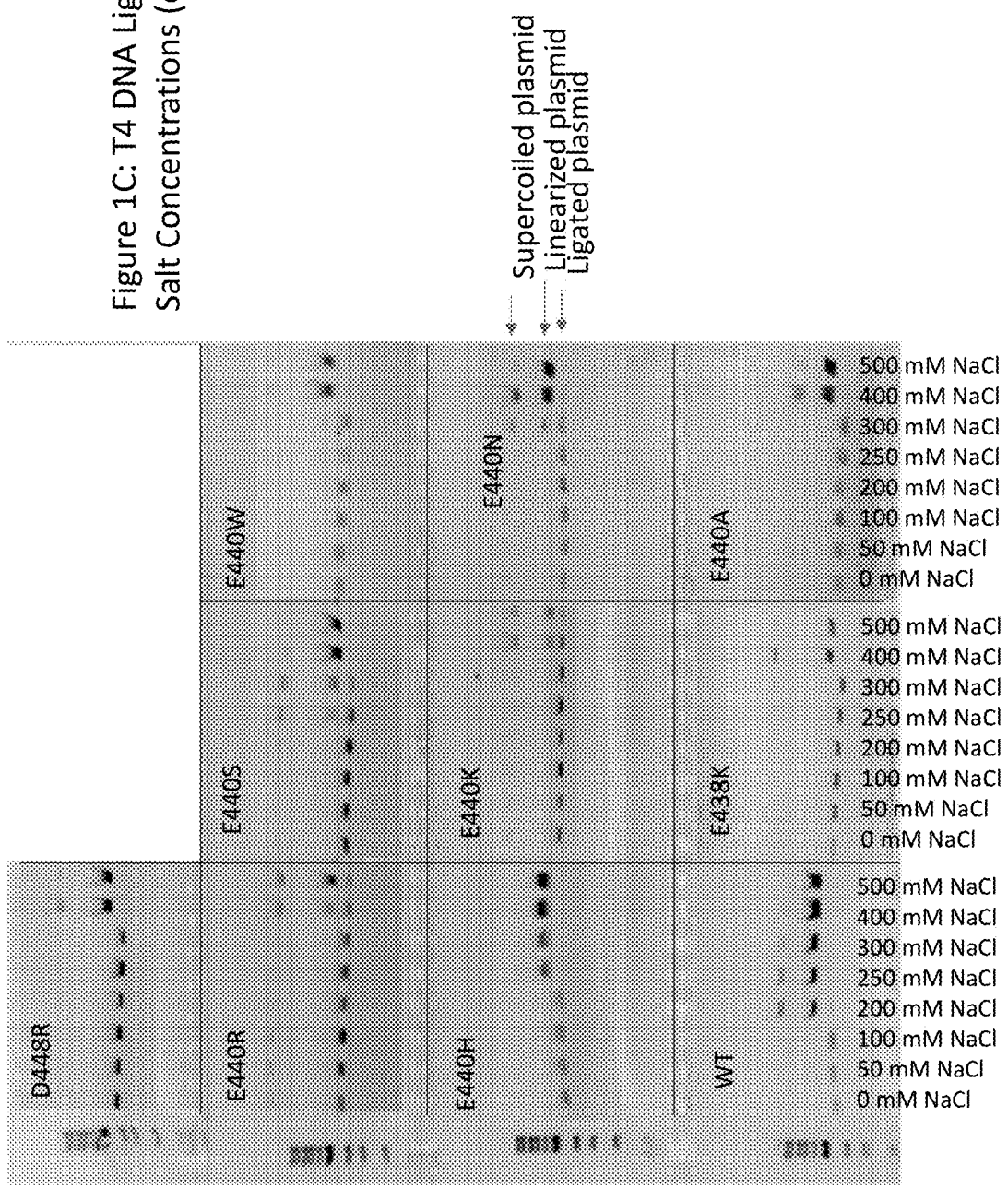

T4 DNA LIGASE VARIANTS WITH INCREASED RESISTANCE TO SALT

BACKGROUND

DNA ligases are integral repair proteins in living organisms that catalyze the repair of single-stranded breaks in duplex DNA. T4 DNA ligase utilizes the energy of the biomolecule ATP to repair nicked double-stranded DNA and also to join double-stranded DNA that has complementary single-strand overhangs (sticky or cohesive ends), as well as blunt-ended fragments, making it a useful tool for combining smaller DNA fragments to create double-stranded DNA constructs in vitro.

DNA ligases form phosphodiester bonds between duplex nucleic acid fragments at the intersection of juxtaposed 5' phosphate and 3' hydroxyl termini. By designing complementary overhangs between each of the double-stranded fragments, ligation can be directed to be both positionally specific and directionally oriented. This allows for specific integration of DNA or RNA fragments into larger vectors to meet the needs of molecular biology research. Out of the commercially available ligases, T4 DNA Ligase is a versatile enzyme that catalyzes the bond joining duplex DNA or RNA at both overhanging ends and blunt ends, has a rapid ligation speed, and via ligation, repairs the mismatches that exist in nicked DNA. Because it is the backbone of many molecular biology protocols and is in constant demand, it generates a large share of the revenue for many life science products companies due to its significance in the molecular biology reagent market.

Typically, wild type (WT) T4 DNA ligase is inhibited by the presence of salt, such as sodium chloride, in the reaction buffer; with complete inhibition of ligation visible in most circumstances at or above 200 mM salt concentrations. Because it is not uncommon for salt contaminants to be present in the insert and vector samples of ligation reactions, purification steps are often required prior to performing ligation. Such added purification steps add time and complexity to experiments, and purification procedures often result in loss of sample—which may be significant. In addition, there is potential for multiple procedures to be combined with ligation in one reaction vessel if ligase is not inhibited by the salt in buffers typically required for using other enzymes. T4 DNA ligase variants with enhanced tolerance to salt in the reaction mixture have a multitude of molecular biology applications. There is therefore a significant need for a ligase that can operate in a high salt environment.

SUMMARY

The invention relates to T4 DNA ligase variants exhibiting increased tolerance to the presence of salt (including NaCl, KCl and other salts) in the reaction mixture, compared to wild-type T4 DNA ligase. The following T4 DNA ligase mutants (with a substitution at the position indicated and wherein each mutant's amino acid sequence is the sequence identification number following the indicated substitution, and wherein a DNA sequence for each such mutant is the odd-numbered sequence identification number in the sequence listing preceding the amino acid sequence identification number of each mutant) were identified as having such increased tolerance to the presence of NaCl: E88K (SEQ ID NO: 4), E132K (SEQ ID NO: 6), E222K (SEQ ID NO: 8), K306E (SEQ ID NO: 10), D340R (SEQ ID NO: 12), K365E (SEQ ID NO: 14), D371A (SEQ ID NO: 16), D371G (SEQ ID NO: 18), D371H (SEQ ID NO: 20), D371I (SEQ ID NO: 22), D371K (SEQ ID NO: 24), D371L (SEQ ID NO: 26), D371M (SEQ ID NO: 28), D371R (SEQ ID NO: 30), D371T (SEQ ID NO: 32), D371Y (SEQ ID NO: 34), E438K (SEQ ID NO: 36), E440A (SEQ ID NO: 38), E440H (SEQ ID NO: 40), E440K (SEQ ID NO: 42), E440N (SEQ ID NO: 44), E440R (SEQ ID NO: 46), E440S (SEQ ID NO: 48), E440W (SEQ ID NO: 50) and D448R (SEQ ID NO: 52).

The full sequences for each of these variants are set forth in the sequence listing following the descriptive portion of the specification. The invention also includes variants which are combinations of one or more of these mutation sites, such that some such variants may have two of these mutation sites, or three of more of these mutation sites.

The invention further includes T4 DNA ligase mutant amino acid sequences with at least one of the mutations above, but wherein the remainder of the T4 DNA ligase mutant amino acid sequence only has conservative substitutions such that the molecule has at least 70%, 80%, 90%, 95%, 96%, 97%, 98% or 99% identity to the corresponding T4 DNA ligase mutant amino acid sequence in the sequence listing (hereinafter referred to as "Variant Sequences").

The invention further includes the DNA sequences preceding each of the amino acid sequences for the mutants above (i.e., respectively, the odd numbered SEQ ID NOS from SEQ ID NO: 3 to SEQ ID NO: 51) and further includes the foregoing DNA sequences and other degenerate nucleic acid sequences (collectively the "Degenerate Nucleic Acid Sequences") encoding (i) each of the above T4 DNA ligase mutants, and (ii) the amino acid sequences of any of the Variant Sequences.

The invention further includes vectors incorporating any Degenerate Nucleic Acid Sequences; and cells transformed with any such vectors or Degenerate Nucleic Acid Sequences and capable of expressing any of the above T4 DNA ligase mutant amino acid sequences or Variant Sequences.

The invention further includes a composition or a kit comprising any of the above T4 DNA ligase mutant amino acid sequences or Variant Sequences, Degenerate Nucleic Acid Sequences, or vectors incorporating such Degenerate Nucleic Acid Sequences. The invention also includes a process of amplifying a target nucleic acid, wherein any of the above T4 DNA ligase mutants or Variant Sequences are employed in a reaction mixture designed to amplify a target nucleic acid, and subjecting the reagent mixture to conditions for amplification of the target nucleic acid.

The above mutant T4 DNA ligase mutants have greater activity in increased salt concentrations, in amplifying target DNA sequences compared with wild type, and the Variant Sequences are also expected to have such greater activity.

BRIEF DESCRIPTION OF THE DRAWINGS

FIGS. 1A to 1C show agarose gel (1.2%) images depicting ligation of a DNA substrate, from sequential testing of ligase activity in null and then seven different NaCl concentrations (i.e., NaCl concentrations where 0 mM, 50 mM, 100 mM, 200 mM, 250 mM, 300 mM, 400 mM, and 500 mM), wherein the reaction mixture was incubated for 60 minutes at 16° C. FIG. 1A shows WT T4 DNA Ligase and T4 DNA Ligase variants E88K (SEQ ID NO: 4), E132K (SEQ ID NO: 6), E222K (SEQ ID NO: 8), K306E (SEQ ID NO: 10), D340R (SEQ ID NO: 12), K365E (SEQ ID NO: 14), D371A (SEQ ID NO: 16), and D371G (SEQ ID NO: 18). FIG. 1B shows WT T4 DNA Ligase and T4 DNA Ligase variants D371H (SEQ ID NO: 20), D371I (SEQ ID NO: 22), D371K (SEQ ID NO: 24), D371L (SEQ ID NO: 26), D371M (SEQ ID NO: 28), D371R (SEQ ID NO: 30), D371T (SEQ ID NO: 32), and D371Y (SEQ ID NO: 34). FIG. 1C shows WT T4 DNA Ligase and T4 DNA Ligase variants E438K (SEQ ID NO: 36), E440A (SEQ ID NO: 38), E440H (SEQ ID NO: 40), E440K (SEQ ID NO: 42), E440N (SEQ ID NO: 44), E440R (SEQ ID NO: 46), E440S (SEQ ID NO: 48), E440W (SEQ ID NO: 50) and D448R (SEQ ID NO: 52).

DETAILED DESCRIPTION

The term "biologically active fragment" refers to any fragment, derivative, homolog or analog of a T4 DNA ligase mutant that possesses in vivo or in vitro activity that is characteristic of that biomolecule; including, for example, ligase activity or repairing via ligation the mismatches that exist in nicked DNA. In some embodiments, the biologically active fragment, derivative, homolog or analog of the mutant T4 DNA ligase possesses any degree of the biological activity of the mutant T4 DNA ligase in any in vivo or in vitro assay of interest.

In some embodiments, the biologically active fragment can optionally include any number of contiguous amino acid residues of the mutant T4 DNA ligase. The invention also includes the polynucleotides encoding any such biologically active fragment.

Biologically active fragments can arise from post transcriptional processing or from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, plant, insect or mammalian cells.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) supra). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

When referring to a gene, "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region. As nonlimiting examples, a mutant gene can be a gene that has an insertion within the promoter region that can either increase or decrease expression of the gene; can be a gene that has a deletion, resulting in production of a nonfunctional protein, truncated protein, dominant negative protein, or no protein; or, can be a gene that has one or more point mutations leading to a change in the amino acid of the encoded protein or results in aberrant splicing of the gene transcript.

The terms "mutant T4 DNA ligase of the invention" and "mutant T4 DNA ligase" when used in this Detailed Description section refer to, depending on the context, collectively or individually, the mutant T4 DNA Ligase polypeptides tested and exhibiting significant ligation activity in the presence of salt concentrations sufficient to significantly decrease the ligation activity of the wild type T4 DNA Ligase, which are: E88K (SEQ ID NO: 4), E132K (SEQ ID NO: 6), E222K (SEQ ID NO: 8), K306E (SEQ ID NO: 10), D340R (SEQ ID NO: 12), K365E (SEQ ID NO: 14), D371A (SEQ ID NO: 16), D371G (SEQ ID NO: 18), D371H (SEQ ID NO: 20), D371I (SEQ ID NO: 22), D371K (SEQ ID NO: 24), D371L (SEQ ID NO: 26), D371M (SEQ ID NO: 28), D371R (SEQ ID NO: 30), D371T (SEQ ID NO: 32), D371Y (SEQ ID NO: 34), E438K (SEQ ID NO: 36), E440A (SEQ ID NO: 38), E440H (SEQ ID NO: 40), E440K (SEQ ID NO: 42), E440N (SEQ ID NO: 44), E440R (SEQ ID NO: 46), E440S (SEQ ID NO: 48), E440W (SEQ ID NO: 50) and D448R (SEQ ID NO: 52).

and/or Variant Sequences and/or Degenerate Nucleic Acid Sequences, as those terms are defined in the Summary section.

"Naturally-occurring" or "wild-type" refers to the form found in nature. For example, a naturally occurring or wild-type polypeptide or polynucleotide sequence is a sequence present in an organism, which has not been intentionally modified by human manipulation.

The terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 units in length (nucleotide bases or amino acids).

In some embodiments, the invention relates to methods (and related kits, systems, apparatuses and compositions) for performing a ligation reaction comprising or consisting of contacting a mutant T4 DNA ligase or a biologically active fragment thereof with a nucleic acid template in the presence of one or more nucleotides, and ligating at least one of the one or more nucleotides using the mutant T4 DNA ligase or the biologically active fragment thereof.

In some embodiments, the method can include ligating a double stranded RNA or DNA polynucleotide strand into a circular molecule. In some embodiments, the method can further include detecting a signal indicating the ligation by using a sensor. In some embodiments, the sensor is an ISFET. In some embodiments, the sensor can include a detectable label or detectable reagent within the ligating reaction.

In some embodiments, the invention relates to methods (and related kits, systems, apparatus and compositions) for performing rolling circle amplification (see U.S. Pat. No. 5,714,320, incorporated by reference) of a nucleic acid, using the mutant T4 DNA ligase as the enzyme in the ligation steps of the amplification process. The amplifying includes amplifying the nucleic acid in solution, as well as clonally amplifying the nucleic acid on a solid support such as a nucleic acid bead, flow cell, nucleic acid array, or wells present on the surface of the solid support.

Making Mutant T4 DNA Ligase

The mutant T4 DNA ligase of the invention can be expressed in any suitable host system, including a bacterial, yeast, fungal, baculovirus, plant or mammalian host cell. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

For baculovirus expression, insect cell lines derived from Lepidopterans (moths and butterflies), such as *Spodoptera frugiperda*, are used as host. Gene expression is under the control of a strong promoter, e.g., pPolh.

Plant expression vectors are based on the Ti plasmid of *Agrobacterium tumefaciens*, or on the tobacco mosaic virus (TMV), potato virus X, or the cowpea mosaic virus. A commonly used constitutive promoter in plant expression vectors is the cauliflower mosaic virus (CaMV) 35S promoter.

For mammalian expression, cultured mammalian cell lines such as the Chinese hamster ovary (CHO), COS, including human cell lines such as HEK and HeLa may be used to produce the mutant T4 DNA ligase. Examples of mammalian expression vectors include the adenoviral vectors, the pSV and the pCMV series of plasmid vectors, vaccinia and retroviral vectors, as well as baculovirus. The promoters for cytomegalovirus (CMV) and SV40 are commonly used in mammalian expression vectors to drive gene expression. Non-viral promoters, such as the elongation factor (EF)-1 promoter, are also known.

The control sequence for the expression may also be a suitable transcription terminator sequence, that is, a sequence recognized by a host cell to terminate transcription. The terminator sequence is operably linked to the 3' terminus of the nucleic acid sequence encoding the polypeptide. Any terminator which is functional in the host cell of choice may be used.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

Terminators for insect, plant and mammalian host cells are also well known.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Signal peptides for other host cell systems are also well known.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the mutant T4 DNA ligase relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Regulatory systems for other host cells are also well known.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Another embodiment includes a recombinant expression vector comprising a polynucleotide encoding an engineered mutant T4 DNA ligase or a variant thereof, and one or more expression regulating regions such as a promoter and a terminator, and a replication origin, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the mutant T4 DNA ligase at such sites. Alternatively, the nucleic acid sequences of the mutant T4 DNA ligase may be expressed by inserting the nucleic acid sequences or a nucleic acid construct comprising the sequences into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the mutant T4 DNA ligase polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector herein preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*. Selectable markers for insect, plant and mammalian cells are also well known.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori, or the origins of replication of plasmids pBR322, pUC19, pACYC177 (which plasmid has the P15A ori), or pACYC184 permitting replication in *E. coli*, and pUB110, pE194, pTA1060, or pAM31 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the mutant T4 DNA ligase may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Expression vectors for the mutant T4 DNA ligase polynucleotide are commercially available. Suitable commercial expression vectors include p3xFLAG™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

Suitable host cells for expression of a polynucleotide encoding the mutant T4 DNA ligase, are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the mutant T4 DNA ligase may be introduced into cells by various methods known in the art. Techniques include among others, electroporation, biolistic particle bombardment, liposome mediated transfection, calcium chloride transfection, and protoplast fusion. Various methods for introducing polynucleotides into cells are known to the skilled artisan.

Polynucleotides encoding the mutant T4 DNA ligase can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., and Operon Technologies Inc., Alameda, Calif.

Engineered the mutant T4 DNA ligase expressed in a host cell can be recovered from the cells and or the culture medium using any one or more of the well-known techniques for protein purification, including, among others, lysozyme treatment, sonication, filtration, salting-out, ultracentrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the mutant T4 DNA ligase include, among others, reverse phase chromatography high performance liquid chromatography, ion exchange chromatography, gel electrophoresis, and affinity chromatography. Conditions for purification will depend, in part, on factors such as net charge, hydrophobicity, hydrophilicity, molecular weight, molecular shape, and will be apparent to those having skill in the art.

In some embodiments, affinity techniques may be used to isolate the mutant T4 DNA ligase. For affinity chromatography purification, any antibody which specifically binds the mutant T4 DNA ligase may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

Example of Making T4 DNA Ligase Mutants

T4 DNA ligase mutants were generated by conventional inverse PCR mutagenesis. All mutants were sequenced verified, expressed in *E. Coli*, and purified. All T4 DNA ligase mutants and the wild type have an added six membered C-terminal His tag for ease of purification, preceded by the sequence: GLGSGSSG (SEQ ID NO: 53).

Ligation substrate was prepared by the following procedure:

The DNA vector substrate used was pUC19 (New England Bio Labs, catalog number N3041S). Commercially available pUC19 is a double stranded circle plasmid that is 2686 base pairs long. The plasmid was digested with BsaI-HF®v2 (New England Bio Labs, catalog number R3733S) which has a recognition sequence of 5'-GGTCTC(N1)/(N5)-3' and makes one cut in the plasmid pUC19, creating a linear piece of DNA with cohesive ends. 5 µl of puC19 at a concentration of 1 mg/ml was combined with 2.5 µl of 20,000 units/ml BsaI-HF®v2, 5 µl 10× rCutSmart™ Buffer (New England Bio Labs, catalog number B6004S) (50 mM Potassium Acetate, 20 mM Tris-acetate, 10 mM Magnesium Acetate, 100 µg/ml Recombinant Albumin), and 35 µl of water incubated at 37° C. for one hour, then heat-inactivated incubated at 80° C. for 20 minutes. The final product was then diluted with water to a concentration of 10 ng/µl.

The ligation screening procedure was performed as follows. Stock concentration of each ligase sample, wild-type or variant was 100 ng/µl. Initial screening tested all variants en masse, comparing mutant to wild-type activity in reaction mixtures containing 100 mM and 200 mM of NaCl.

For each reaction, 200 ng of enzyme was pipetted, in duplicate, into individual wells of a PCR plate. To each was added a master mix consisting of 1×T4 DNA Ligase Reaction Buffer (New England Biolabs, catalog number B0202A: 50 mM Tris-HCl, 10 mM MgCl$_2$, 1 mM ATP, 10 mM DTT), 5 ng substrate (pUC19 digested with BsaI-HF®v2), a volume of 5M NaCl necessary to the desired final salt concentration, and sufficient water to make the total volume per reaction 20 µl. The reactions were incubated at 16° C. for 30 minutes. After the 30-minute incubation period the reactions received a heat shock of 80° C. for 2 minutes to stop any further activity. Additionally, 4 µl of stop solution (120 mM EDTA, 30% glycerol, 50 mM Tris-HCl pH 8.0, 0.0125% bromophenol blue, 0.1% SDS, and 5× Gel Red Nucleic Acid Stain (Biotium, Fremont, Calif.)) was added to every reaction.

Gel electrophoresis was performed using 1.2% agarose gels run at 180V for 35 minutes. Each gel displayed a wild-type T4 DNA ligase sample and 47 variant T4 DNA ligase samples, in duplicate. Variants that suggested greater salt resistance by completing ligation more effectively than WT at any concentration were identified for secondary screening and confirmation.

Secondary screening involved challenging each previously selected mutant, as well as wild-type, with a titration of salt. The NaCl concentrations tested in this titration were: 0 mM, 50 mM, 100 mM, 200 mM, 250 mM, 300 mM, 400 mM, and 500 mM. Each reaction contained 400 ng total protein (4 µl stock protein), plus 16 µl of a master mix consisting of 1×T4 DNA Ligase Reaction Buffer (New England Biolabs, catalog number B0202A: 50 mM Tris-HCl, 10 mM MgCl$_2$, 1 mM ATP, 10 mM DTT), 10 ng substrate, the required volume 5M NaCl to achieve each salt concentration, and sufficient water to achieve total volume per reaction of 20 µl. The ligation reactions were incubated at 16° C. for 60 minutes, then subjected to a heat shock at 80° C. for 2 minutes to stop any further activity. Finally, 6 µl of stop solution (120 mM EDTA, 30% glycerol, 50 mM Tris-HCl pH 8.0, 0.0125% bromophenol blue, 0.1% SDS, and 5× Gel Red Nucleic Acid Stain (Biotium, Fremont, Calif.)) was added to every reaction.

Gel electrophoresis was performed using 1.2% agarose gels run at 180V for 35 minutes. Each gel displays a wild-type T4 DNA ligase sample and eleven variant T4 DNA ligase samples, each at salt ranging from 0-500 mM over 8 lanes. Variants exhibiting increased tolerance to the presence of salt in the reaction mixture compared to wild-type T4 DNA Ligase were identified, with results shown in FIG. 1; and are also listed in Table 1, which shows each mutants' tolerance limits for salt concentration while retaining activity. These variants were E88K, E132K, E222K, K306E, D340R, D371H, K365E, E438K, D448R, D371A, D371G, D371I, D371K, D371L, D371M, D371R, D371T, D371Y, E440A, E440H, E440K, E440N, E440R, E440S, E440W and D448R Composite agarose gel images showing the ligation activity of variants compared to wild-type are in FIG. 1. The images show double strand ligated super coiled plasmid as the lowest band, un-ligated linearized plasmid as the middle band, and a faint upper band that is supercoiled single strand ligated nicked circular DNA. As salt concentration increases from left to right on each ligation series, the ligated substrate eventually disappears and only un-ligated substrate and supercoiled nicked circular DNA remain as the ligase is inactivated by the presence of excess NaCl in the reaction buffer.

TABLE 1

Molar Salt Concentration Limits of Engineered T4 DNA Ligase Variants

| Mutation | NaCl (mM) |
| --- | --- |
| E88K | 250 |
| E132K | 250 |

TABLE 1-continued

Molar Salt Concentration Limits of Engineered T4 DNA Ligase Variants

| Mutation | NaCl (mM) |
| --- | --- |
| E222K | 250 |
| K306E | 250 |
| D340R | 250 |
| K365E | 250 |
| D371A | 250 |
| D371G | 400 |
| D371H | 250 |
| D371I | 300 |
| D371K | 300 |
| D371L | 300 |
| D371M | 300 |
| D371R | 400 |
| D371T | 300 |
| D371Y | 300 |
| E440S | 250 |
| E438K | 200 |
| E440A | 300 |
| E440H | 400 |
| E440N | 300 |
| E440K | 400 |
| E440R | 400 |
| E440W | 300 |
| D448R | 300 |

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, including but not limited to Variant Sequences, and that such modifications and variations are considered to be within the scope of this invention as defined by the appended claims.

```
T4 DNA Ligase CH Wild Type DNA
                                                         SEQ ID NO: 1
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960
```

```
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTGATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAATTATTATATTGGAAAAATTCTAGAGTGCGAA  1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH Wild Type Protein
SEQ ID NO: 2
```
  1 MILKILNEIASIGSTKQKQAILEKNKDNELLKRVYRLTYSRGLQYYIKKWPKPGIATQSF   60
 61 GMLTLTDMLDFIEFTLATRKLTGNAAIEELTGYITDGKKDDVEVLRRVMMRDLECGASVS  120
121 IANKVWPGLIPEQPQMLASSYDEKGINKNIKFPAFAQLKADGARCFAEVRGDELDDVRLL  180
181 SRAGNEYLGLDLLKEELIKMTAEARQIHPEGVLIDGELVYHEQVKKEPEGLDFLFDAYPE  240
241 NSKAKEFAEVAESRTASNGIANKSLKGTISEKEAQCMKFQVWDYVPLVEIYSLPAFRLKY  300
301 DVRFSKLEQMTSGYDKVILIENQVVNNLDEAKVIYKKYIDQGLEGIILKNIDGLWENARS  360
361 KNLYKFKEVIDVDLKIVGIYPHRKDPTKAGGFILESECGKIKVNAGSGLKDKAGVKSHEL  420
421 DRTRIMENQNYYIGKILECECNGWLKSDGRTDYVKLFLPIAIRLREDKTKANTFEDVFGD  480
481 FHEVTGLGSGSSGHHHHHH*                                         499
```

T4 DNA Ligase CH E88K DNA
SEQ ID NO: 3
```
  1 ATGATTCTTAAAATTCTGAACGAAATAGCATCTATTGGTTCAACTAAACAGAAGCAAGCA   60
 61 ATTCTTGAAAAGAATAAAGATAATGAATTGCTTAAACGAGTATATCGTCTGACTTATTCT  120
121 CGTGGGTTACAGTATTATATCAAGAAATGGCCTAAACCTGGTATTGCTACCCAGAGTTTT  180
181 GGAATGTTGACTCTTACCGATATGCTTGACTTCATTGAATTCACATTAGCTACTCGGAAA  240
241 TTGACTGGAAATGCAGCAATTAAAGAATTAACTGGATATATCACCGATGGTAAAAAAGAT  300
301 GATGTTGAAGTTTTGCGTCGAGTGATGATGCGAGACCTTGAATGTGGTGCTTCAGTATCT  360
361 ATTGCAAACAAAGTTTGGCCAGGTTTAATTCCTGAACAACCTCAAATGCTCGCAAGTTCT  420
421 TATGATGAAAAGGCATTAATAAGAATATCAAATTTCCAGCCTTTGCTCAGTTAAAAGCT   480
481 GATGGAGCTCGGTGTTTTGCTGAAGTTAGAGGTGATGAATTAGATGATGTTCGTCTTTTA  540
541 TCACGAGCTGGTAATGAATATCTAGGATTAGATCTTCTTAAGGAAGAGTTAATTAAAATG  600
601 ACCGCTGAAGCCCGCCAGATTCATCCAGAAGGTGTGTTGATTGATGGCGAATTGGTATAC  660
661 CATGAGCAAGTTAAAAAGGAGCCAGAAGGCCTAGATTTTCTTTTTGATGCTTATCCTGAA  720
721 AACAGTAAAGCTAAAGAATTCGCCGAAGTAGCTGAATCACGTACTGCTTCTAATGGAATC  780
781 GCCAATAAATCTTTAAAGGGAACCATTTCTGAAAAAGAAGCACAATGCATGAAGTTTCAG  840
841 GTCTGGGATTATGTCCCGTTGGTAGAAATATACAGTCTTCCTGCATTTCGTTTGAAATAT  900
901 GATGTACGTTTTTCTAAACTAGAACAAATGACATCTGGATATGATAAAGTAATTTTAATT  960
961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTGATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
```

-continued

```
1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH E88K Protein

SEQ ID NO: 4

```
  1 MILKILNEIASIGSTKQKQAILEKNKDNELLKRVYRLTYSRGLQYYIKKWPKPGIATQSF   60

61 GMLTLTDMLDFIEFTLATRKLTGNAAIKELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIDVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                          499
```

T4 DNA Ligase CH E132K DNA

SEQ ID NO: 5

```
   1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTAAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

```
T4 DNA Ligase CH E132K Protein
                                                        SEQ ID NO: 6
   1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPKQPQMLASSYDEKGINKNIKFPAFAQLKADGARCFAEVRGDELDDVRLL   180

181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIDVDLKIVGIYPHRKDPTKAGGFILESECGKIKVNAGSGLKDKAGVKSHEL   420

421 DRTRIMENQNYYIGKILECECNGWLKSDGRTDYVKLFLPIAIRLREDKTKANTFEDVFGD   480

481 FHEVTGLGSGSSGHHHHHH*                                          499

T4 DNA Ligase CH E222K DNA
                                                        SEQ ID NO: 7
   1 ATGATTCTTAAAATTCTGAACGAAATAGCATCTATTGGTTCAACTAAACAGAAGCAAGCA    60

61 ATTCTTGAAAAGAATAAAGATAATGAATTGCTTAAACGAGTATATCGTCTGACTTATTCT   120

121 CGTGGGTTACAGTATTATATCAAGAAATGGCCTAAACCTGGTATTGCTACCCAGAGTTTT   180

181 GGAATGTTGACTCTTACCGATATGCTTGACTTCATTGAATTCACATTAGCTACTCGGAAA   240

241 TTGACTGGAAATGCAGCAATTGAGGAATTAACTGGATATATCACCGATGGTAAAAAAGAT   300

301 GATGTTGAAGTTTTGCGTCGAGTGATGATGCGAGACCTTGAATGTGGTGCTTCAGTATCT   360

361 ATTGCAAACAAAGTTTGGCCAGGTTTAATTCCTGAACAACCTCAAATGCTCGCAAGTTCT   420

421 TATGATGAAAAAGGCATTAATAAGAATATCAAATTTCCAGCCTTTGCTCAGTTAAAAGCT   480

481 GATGGAGCTCGGTGTTTTGCTGAAGTTAGAGGTGATGAATTAGATGATGTTCGTCTTTTA   540

541 TCACGAGCTGGTAATGAATATCTAGGATTAGATCTTCTTAAGGAAGAGTTAATTAAAATG   600

601 ACCGCTGAAGCCCGCCAGATTCATCCAGAAGGTGTGTTGATTGATGGCGAATTGGTATAC   660

661 CATAAACAAGTTAAAAAGGAGCCAGAAGGCCTAGATTTTCTTTTTGATGCTTATCCTGAA   720

721 AACAGTAAAGCTAAAGAATTCGCCGAAGTAGCTGAATCACGTACTGCTTCTAATGGAATC   780

781 GCCAATAAATCTTTAAAGGGAACCATTTCTGAAAAAGAAGCACAATGCATGAAGTTTCAG   840

841 GTCTGGGATTATGTCCCGTTGGTAGAAATATACAGTCTTCCTGCATTTCGTTTGAAATAT   900

901 GATGTACGTTTTTCTAAACTAGAACAAATGACATCTGGATATGATAAAGTAATTTTAATT   960

961 GAAAACCAGGTAGTAAATAACCTAGATGAAGCTAAGGTAATTTATAAAAAGTATATTGAC  1020

1021 CAAGGTCTTGAAGGTATTATTCTCAAAAATATCGATGGATTATGGGAAAATGCTCGTTCA  1080

1081 AAAAATCTTTATAAATTTAAAGAAGTAATTGATGTTGATTTAAAAATTGTAGGAATTTAT  1140

1141 CCTCACCGTAAAGACCCTACTAAAGCGGGTGGATTTATTCTTGAGTCAGAGTGTGGAAAA  1200

1201 ATTAAGGTAAATGCTGGTTCAGGCTTAAAAGATAAAGCCGGTGTAAAATCGCATGAACTT  1260

1261 GACCGTACTCGCATTATGGAAAACCAAAATTATTATATTGGAAAAATTCTAGAGTGCAA  1320

1321 TGCAACGGTTGGTTAAAATCTGATGGCCGCACTGATTACGTTAAATTATTTCTTCCGATT  1380

1381 GCGATTCGTTTACGTGAAGATAAAACTAAAGCTAATACATTCGAAGATGTATTTGGTGAT  1440

1441 TTTCATGAGGTAACTGGTCTAGGTTCTGGCAGTTCAGGTCATCACCACCATCATCACTAA  1500

T4 DNA Ligase CH E222K Protein
                                                        SEQ ID NO: 8
   1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180
```

-continued

```
181 SRAGNEYLGLDLLKEELIKMTAEARQIHPEGVLIDGELVYHKQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIDVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                         499
```

T4 DNA Ligase CH K306E DNA

SEQ ID NO: 9

```
   1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATACACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTGAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH K306E Protein

SEQ ID NO: 10

```
   1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300
```

-continued

```
301 DVRFSELEQMTSGYDKVILIENQVVNNLDEAKVIYKKYIDQGLEGIILKNIDGLWENARS    360
361 KNLYKFKEVIDVDLKIVGIYPHRKDPTKAGGFILESECGKIKVNAGSGLKDKAGVKSHEL    420
421 DRTRIMENQNYYIGKILECECNGWLKSDGRTDYVKLFLPIAIRLREDKTKANTFEDVFGD    480
481 FHEVTGLGSGSSGHHHHHH*                                            499
```

T4 DNA Ligase CH D340R DNA
SEQ ID NO: 11

```
   1 ATGATTCTTAAAATTCTGAACGAAATAGCATCTATTGGTTCAACTAAACAGAAGCAAGCA    60
  61 ATTCTTGAAAAGAATAAAGATAATGAATTGCTTAAACGAGTATATCGTCTGACTTATTCT   120
 121 CGTGGGTTACAGTATTATATCAAGAAATGGCCTAAACCTGGTATTGCTACCCAGAGTTTT   180
 181 GGAATGTTGACTCTTACCGATATGCTTGACTTCATTGAATTCACATTAGCTACTCGGAAA   240
 241 TTGACTGGAAATGCAGCAATTGAGGAATTAACTGGATATATCACCGATGGTAAAAAAGAT   300
 301 GATGTTGAAGTTTTGCGTCGAGTGATGATGCGAGACCTTGAATGTGGTGCTTCAGTATCT   360
 361 ATTGCAAACAAAGTTTGGCCAGGTTTAATTCCTGAACAACCTCAAATGCTCGCAAGTTCT   420
 421 TATGATGAAAAAGGCATTAATAAGAATATCAAATTTCCAGCCTTTGCTCAGTTAAAAGCT   480
 481 GATGGAGCTCGGTGTTTTGCTGAAGTTAGAGGTGATGAATTAGATGATGTTCGTCTTTTA   540
 541 TCACGAGCTGGTAATGAATATCTAGGATTAGATCTTCTTAAGGAAGAGTTAATTAAAATG   600
 601 ACCGCTGAAGCCCGCCAGATTCATCCAGAAGGTGTGTTGATTGATGGCGAATTGGTATAC   660
 661 CATGAGCAAGTTAAAAAGGAGCCAGAAGGCCTAGATTTTCTTTTTGATGCTTATCCTGAA   720
 721 AACAGTAAAGCTAAAGAATTCGCCGAAGTAGCTGAATCACGTACTGCTTCTAATGGAATC   780
 781 GCCAATAAATCTTTAAAGGGAACCATTTCTGAAAAAGAAGCACAATGCATGAAGTTTCAG   840
 841 GTCTGGGATTATGTCCCGTTGGTAGAAATATACAGTCTTCCTGCATTTCGTTTGAAATAT   900
 901 GATGTACGTTTTTCTAAACTAGAACAAATGACATCTGGATATGATAAAGTAATTTTAATT   960
 961 GAAAACCAGGTAGTAAATAACCTAGATGAAGCTAAGGTAATTTATAAAAAGTATATTCGT  1020
1021 CAAGGTCTTGAAGGTATTATTCTCAAAAATATCGATGGATTATGGGAAAATGCTCGTTCA  1080
1081 AAAAATCTTTATAAATTTAAAGAAGTAATTGATGTTGATTTAAAAATTGTAGGAATTTAT  1140
1141 CCTCACCGTAAAGACCCTACTAAAGCGGGTGGATTTATTCTTGAGTCAGAGTGTGGAAAA  1200
1201 ATTAAGGTAAATGCTGGTTCAGGCTTAAAAGATAAAGCCGGTGTAAAATCGCATGAACTT  1260
1261 GACCGTACTCGCATTATGGAAAACCAAATTATTATATTGGAAAAATTCTAGAGTGCGAA   1320
1321 TGCAACGGTTGGTTAAAATCTGATGGCCGCACTGATTACGTTAAATTATTTCTTCCGATT  1380
1381 GCGATTCGTTTACGTGAAGATAAAACTAAAGCTAATACATTCGAAGATGTATTTGGTGAT  1440
1441 TTTCATGAGGTAACTGGTCTAGGTTCTGGCAGTTCAGGTCATCACCACCATCATCACTAA  1500
```

T4 DNA Ligase CH D340R Protein
SEQ ID NO: 12

```
   1 MILKILNEIASIGSTKQKQAILEKNKDNELLKRVYRLTYSRGLQYYIKKWPKPGIATQSF    60
  61 GMLTLTDMLDFIEFTLATRKLTGNAAIEELTGYITDGKKDDVEVLRRVMMRDLECGASVS   120
 121 IANKVWPGLIPEQPQMLASSYDEKGINKNIKFPAFAQLKADGARCFAEVRGDELDDVRLL   180
 181 SRAGNEYLGLDLLKEELIKMTAEARQIHPEGVLIDGELVYHEQVKKEPEGLDFLFDAYPE   240
 241 NSKAKEFAEVAESRTASNGIANKSLKGTISEKEAQCMKFQVWDYVPLVEIYSLPAFRLKY   300
 301 DVRFSKLEQMTSGYDKVILIENQVVNNLDEAKVIYKKYIRQGLEGIILKNIDGLWENARS   360
 361 KNLYKFKEVIDVDLKIVGIYPHRKDPTKAGGFILESECGKIKVNAGSGLKDKAGVKSHEL   420
 421 DRTRIMENQNYYIGKILECECNGWLKSDGRTDYVKLFLPIAIRLREDKTKANTFEDVFGD   480
 481 FHEVTGLGSGSSGHHHHHH*                                            499
```

-continued

T4 DNA Ligase CH K365E DNA

SEQ ID NO: 13

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
 241 TTGACTGGAAATGCAGCAATTGAGGAATTAACTGGATATATCACCGATGGTAAAAAAGAT  300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATGAATTTAAAGAAGTAATTGATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAATTATTATATTGGAAAAATTCTAGAGTGCGAA  1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH K365E Protein

SEQ ID NO: 14

```
  1 MILKILNEIASIGSTKQKQAILEKNKDNELLKRVYRLTYSRGLQYYIKKWPKPGIATQSF   60
 61 GMLTLTDMLDFIEFTLATRKLTGNAAIEELTGYITDGKKDDVEVLRRVMMRDLECGASVS  120
121 IANKVWPGLIPEQPQMLASSYDEKGINKNIKFPAFAQLKADGARCFAEVRGDELDDVRLL  180
181 SRAGNEYLGLDLLKEELIKMTAEARQIHPEGVLIDGELVYHEQVKKEPEGLDFLFDAYPE  240
241 NSKAKEFAEVAESRTASNGIANKSLKGTISEKEAQCMKFQVWDYVPLVEIYSLPAFRLKY  300
301 DVRFSKLEQMTSGYDKVILIENQVVNNLDEAKVIYKKYIDQGLEGIILKNIDGLWENARS  360
361 KNLYEFKEVIDVDLKIVGIYPHRKDPTKAGGFILESECGKIKVNAGSGLKDKAGVKSHEL  420
421 DRTRIMENQNYYIGKILECECNGWLKSDGRTDYVKLFLPIAIRLREDKTKANTFEDVFGD  480
481 FHEVTGLGSGSSGHHHHHH*                                         499
```

T4 DNA Ligase CH D371A DNA

SEQ ID NO: 15

```
  1 ATGATTCTTAAAATTCTGAACGAAATAGCATCTATTGGTTCAACTAAACAGAAGCAAGCA   60
 61 ATTCTTGAAAAGAATAAAGATAATGAATTGCTTAAACGAGTATATCGTCTGACTTATTCT  120
121 CGTGGGTTACAGTATTATATCAAGAAATGGCCTAAACCTGGTATTGCTACCCAGAGTTTT  180
181 GGAATGTTGACTCTTACCGATATGCTTGACTTCATTGAATTCACATTAGCTACTCGGAAA  240
```

-continued

```
 241 TTGACTGGAAATGCAGCAATTGAGGAATTAACTGGATATATCACCGATGGTAAAAAGAT  300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTGCAGTTGATTTAAAAATTGTAGGAATTTAT 1140
1141 CCTCACCGTAAAGACCCTACTAAAGCGGGTGGATTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAAATTATTATATTGGAAAAATTCTAGAGTGCGAA 1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH D371A Protein
SEQ ID NO: 16

```
  1 MILKILNEIASIGSTKQKQAILEKNKDNELLKRVYRLTYSRGLQYYIKKWPKPGIATQSF   60
 61 GMLTLTDMLDFIEFTLATRKLTGNAAIEELTGYITDGKKDDVEVLRRVMMRDLECGASVS  120
121 IANKVWPGLIPEQPQMLASSYDEKGINKNIKFPAFAQLKADGARCFAEVRGDELDDVRLL  180
181 SRAGNEYLGLDLLKEELIKMTAEARQIHPEGVLIDGELVYHEQVKKEPEGLDFLFDAYPE  240
241 NSKAKEFAEVAESRTASNGIANKSLKGTISEKEAQCMKFQVWDYVPLVEIYSLPAFRLKY  300
301 DVRFSKLEQMTSGYDKVILIENQVVNNLDEAKVIYKKYIDQGLEGIILKNIDGLWENARS  360
361 KNLYKFKEVIAVDLKIVGIYPHRKDPTKAGGFILESECGKIKVNAGSGLKDKAGVKSHEL  420
421 DRTRIMENQNYYIGKILECECNGWLKSDGRTDYVKLFLPIAIRLREDKTKANTFEDVFGD  480
481 FHEVTGLGSGSSGHHHHHH*                                          499
```

T4 DNA Ligase CH D371G DNA
SEQ ID NO: 17

```
  1 ATGATTCTTAAAATTCTGAACGAAATAGCATCTATTGGTTCAACTAAACAGAAGCAAGCA   60
 61 ATTCTTGAAAAGAATAAAGATAATGAATTGCTTAAACGAGTATATCGTCTGACTTATTCT  120
121 CGTGGGTTACAGTATTATATCAAGAAATGGCCTAAACCTGGTATTGCTACCCAGAGTTTT  180
181 GGAATGTTGACTCTTACCGATATGCTTGACTTCATTGAATTCACATTAGCTACTCGGAAA  240
241 TTGACTGGAAATGCAGCAATTGAGGAATTAACTGGATATATCACCGATGGTAAAAAGAT  300
301 GATGTTGAAGTTTTGCGTCGAGTGATGATGCGAGACCTTGAATGTGGTGCTTCAGTATCT  360
361 ATTGCAAACAAAGTTTGGCCAGGTTTAATTCCTGAACAACCTCAAATGCTCGCAAGTTCT  420
421 TATGATGAAAAGGCATTAATAAGAATATCAAATTTCCAGCCTTTGCTCAGTTAAAAGCT  480
```

```
-continued
 481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGGTGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500

T4 DNA Ligase CH D371G Protein
                                                      SEQ ID NO: 18
   1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIGVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                          499

T4 DNA Ligase CH D371H DNA
                                                      SEQ ID NO: 19
   1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780
```

-continued

```
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTCATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAAATTATTATATTGGAAAAATTCTAGAGTGCGAA 1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH D371H Protein

SEQ ID NO: 20

```
  1 MILKILNEIASIGSTKQKQAILEKNKDNELLKRVYRLTYSRGLQYYIKKWPKPGIATQSF   60
 61 GMLTLTDMLDFIEFTLATRKLTGNAAIEELTGYITDGKKDDVEVLRRVMMRDLECGASVS  120
121 IANKVWPGLIPEQPQMLASSYDEKGINKNIKFPAFAQLKADGARCFAEVRGDELDDVRLL  180
181 SRAGNEYLGLDLLKEELIKMTAEARQIHPEGVLIDGELVYHEQVKKEPEGLDFLFDAYPE  240
241 NSKAKEFAEVAESRTASNGIANKSLKGTISEKEAQCMKFQVWDYVPLVEIYSLPAFRLKY  300
301 DVRFSKLEQMTSGYDKVILIENQVVNNLDEAKVIYKKYIDQGLEGIILKNIDGLWENARS  360
361 KNLYKFKEVIHVDLKIVGIYPHRKDPTKAGGFILESECGKIKVNAGSGLKDKAGVKSHEL  420
421 DRTRIMENQNYYIGKILECECNGWLKSDGRTDYVKLFLPIAIRLREDKTKANTFEDVFGD  480
481 FHEVTGLGSGSSGHHHHHH*                                          499
```

T4 DNA Ligase CH D371I DNA

SEQ ID NO: 21

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
 241 TTGACTGGAAATGCAGCAATTGAGGAATTAACTGGATATATCACCGATGGTAAAAAGAT  300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
```

-continued

```
1021 CAAGGTCTTGAAGGTATTATTCTCAAAAATATCGATGGATTATGGGAAAATGCTCGTTCA 1080

1081 AAAAATCTTTATAAATTTAAAGAAGTAATTATTGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH D371I Protein
SEQ ID NO: 22
```
  1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180

181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIIVDLKIVGIYPHRKDPTKAGGFILESECGKIKVNAGSGLKDKAGVKSHEL   420

421 DRTRIMENQNYYIGKILECECNGWLKSDGRTDYVKLFLPIAIRLREDKTKANTFEDVFGD   480

481 FHEVTGLGSGSSGHHHHHH*                                          499
```

T4 DNA Ligase CH D371K DNA
SEQ ID NO: 23
```
   1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTAAAGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320
```

-continued

```
1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH D371K Protein

SEQ ID NO: 24

```
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIKVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                         499
```

T4 DNA Ligase CH D371L DNA

SEQ ID NO: 25

```
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTTTGGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

```
T4 DNA Ligase CH D371L Protein
                                                SEQ ID NO: 26
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVILVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                          499

T4 DNA Ligase CH D371M DNA
                                                SEQ ID NO: 27
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTATGGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500

T4 DNA Ligase CH D371M Protein
                                                SEQ ID NO: 28
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180
```

```
181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIMVDLKIVGIYPHRKDPTKAGGFILESECGKIKVNAGSGLKDKAGVKSHEL  420

421 DRTRIMENQNYYIGKILECECNGWLKSDGRTDYVKLFLPIAIRLREDKTKANTFEDVFGD  480

481 FHEVTGLGSGSSGHHHHHH*                                          499
```

T4 DNA Ligase CH D371R DNA

SEQ ID NO: 29

```
   1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATACACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTCGTGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAATTATTATATTGGAAAAATTCTAGAGTGCGAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH D371R Protein

SEQ ID NO: 30

```
   1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300
```

-continued

```
301 DVRFSKLEQMTSGYDKVILIENQVVNNLDEAKVIYKKYIDQGLEGIILKNIDGLWENARS  360
361 KNLYKFKEVIRVDLKIVGIYPHRKDPTKAGGFILESECGKIKVNAGSGLKDKAGVKSHEL  420
421 DRTRIMENQNYYIGKILECECNGWLKSDGRTDYVKLFLPIAIRLREDKTKANTFEDVFGD  480
481 FHEVTGLGSGSSGHHHHHH*                                         499
```

T4 DNA Ligase CH D371T DNA

SEQ ID NO: 31

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
 241 TTGACTGGAAATGCAGCAATTGAGGAATTAACTGGATATATCACCGATGGTAAAAAAGAT  300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTACTGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAATTATTATATTGGAAAAATTCTAGAGTGCGAA 1320
1321 TGCAACGGTTGGTTAAAATCTGATGGCCGCACTGATTACGTTAAATTATTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH D371T Protein

SEQ ID NO: 32

```
   1 MILKILNEIASIGSTKQKQAILEKNKDNELLKRVYRLTYSRGLQYYIKKWPKPGIATQSF   60
  61 GMLTLTDMLDFIEFTLATRKLTGNAAIEELTGYITDGKKDDVEVLRRVMMRDLECGASVS  120
 121 IANKVWPGLIPEQPQMLASSYDEKGINKNIKFPAFAQLKADGARCFAEVRGDELDDVRLL  180
 181 SRAGNEYLGLDLLKEELIKMTAEARQIHPEGVLIDGELVYHEQVKKEPEGLDFLFDAYPE  240
 241 NSKAKEFAEVAESRTASNGIANKSLKGTISEKEAQCMKFQVWDYVPLVEIYSLPAFRLKY  300
 301 DVRFSKLEQMTSGYDKVILIENQVVNNLDEAKVIYKKYIDQGLEGIILKNIDGLWENARS  360
 361 KNLYKFKEVITVDLKIVGIYPHRKDPTKAGGFILESECGKIKVNAGSGLKDKAGVKSHEL  420
 421 DRTRIMENQNYYIGKILECECNGWLKSDGRTDYVKLFLPIAIRLREDKTKANTFEDVFGD  480
 481 FHEVTGLGSGSSGHHHHHH*                                         499
```

-continued

T4 DNA Ligase CH D371Y DNA

SEQ ID NO: 33

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
 241 TTGACTGGAAATGCAGCAATTGAGGAATTAACTGGATATATCACCGATGGTAAAAAAGAT  300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTTACGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAATTATTATATTGGAAAAATTCTAGAGTGCGAA  1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH D371Y Protein

SEQ ID NO: 34

```
   1 MILKILNEIASIGSTKQKQAILEKNKDNELLKRVYRLTYSRGLQYYIKKWPKPGIATQSF   60
  61 GMLTLTDMLDFIEFTLATRKLTGNAAIEELTGYITDGKKDDVEVLRRVMMRDLECGASVS  120
 121 IANKVWPGLIPEQPQMLASSYDEKGINKNIKFPAFAQLKADGARCFAEVRGDELDDVRLL  180
 181 SRAGNEYLGLDLLKEELIKMTAEARQIHPEGVLIDGELVYHEQVKKEPEGLDFLFDAYPE  240
 241 NSKAKEFAEVAESRTASNGIANKSLKGTISEKEAQCMKFQVWDYVPLVEIYSLPAFRLKY  300
 301 DVRFSKLEQMTSGYDKVILIENQVVNNLDEAKVIYKKYIDQGLEGIILKNIDGLWENARS  360
 361 KNLYKFKEVIYVDLKIVGIYPHRKDPTKAGGFILESECGKIKVNAGSGLKDKAGVKSHEL  420
 421 DRTRIMENQNYYIGKILECECNGWLKSDGRTDYVKLFLPIAIRLREDKTKANTFEDVFGD  480
 481 FHEVTGLGSGSSGHHHHHH*                                          499
```

T4 DNA Ligase CH E438K DNA

SEQ ID NO: 35

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
```

```
241 TTGACTGGAAATGCAGCAATTGAGGAATTAACTGGATATATCACCGATGGTAAAAAGAT    300

301 GATGTTGAAGTTTTGCGTCGAGTGATGATGCGAGACCTTGAATGTGGTGCTTCAGTATCT    360

361 ATTGCAAACAAAGTTTGGCCAGGTTTAATTCCTGAACAACCTCAAATGCTCGCAAGTTCT    420

421 TATGATGAAAAGGCATTAATAAGAATATCAAATTTCCAGCCTTTGCTCAGTTAAAAGCT    480

481 GATGGAGCTCGGTGTTTTGCTGAAGTTAGAGGTGATGAATTAGATGATGTTCGTCTTTTA    540

541 TCACGAGCTGGTAATGAATATCTAGGATTAGATCTTCTTAAGGAAGAGTTAATTAAAATG    600

601 ACCGCTGAAGCCCGCCAGATTCATCCAGAAGGTGTGTTGATTGATGGCGAATTGGTATAC    660

661 CATGAGCAAGTTAAAAAGGAGCCAGAAGGCCTAGATTTTCTTTTTGATGCTTATCCTGAA    720

721 AACAGTAAAGCTAAAGAATTCGCCGAAGTAGCTGAATCACGTACTGCTTCTAATGGAATC    780

781 GCCAATAAATCTTTAAAGGGAACCATTTCTGAAAAAGAAGCACAATGCATGAAGTTTCAG    840

841 GTCTGGGATTATGTCCCGTTGGTAGAAATATACAGTCTTCCTGCATTTCGTTTGAAATAT    900

901 GATGTACGTTTTTCTAAACTAGAACAAATGACATCTGGATATGATAAAGTAATTTTAATT    960

961 GAAAACCAGGTAGTAAATAACCTAGATGAAGCTAAGGTAATTTATAAAAGTATATTGAC   1020

1021 CAAGGTCTTGAAGGTATTATTCTCAAAAATATCGATGGATTATGGGAAAATGCTCGTTCA   1080

1081 AAAAATCTTTATAAATTTAAAGAAGTAATTGATGTTGATTTAAAAATTGTAGGAATTTAT   1140

1141 CCTCACCGTAAAGACCCTACTAAAGCGGGTGGATTTATTCTTGAGTCAGAGTGTGGAAAA   1200

1201 ATTAAGGTAAATGCTGGTTCAGGCTTAAAAGATAAAGCCGGTGTAAAATCGCATGAACTT   1260

1261 GACCGTACTCGCATTATGGAAAACCAAAATTATTATATTGGAAAAATTCTAAAATGCGAA   1320

1321 TGCAACGGTTGGTTAAAATCTGATGGCCGCACTGATTACGTTAAATTATTCTTCCGATT   1380

1381 GCGATTCGTTTACGTGAAGATAAAACTAAAGCTAATACATTCGAAGATGTATTTGGTGAT   1440

1441 TTTCATGAGGTAACTGGTCTAGGTTCTGGCAGTTCAGGTCATCACCACCATCATCACTAA   1500
```

T4 DNA Ligase CH E438K Protein

SEQ ID NO: 36

```
  1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180

181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIDVDLKIVGIYPHRKDPTKAGGFILESECGKIKVNAGSGLKDKAGVKSHEL   420

421 DRTRIMENQNYYIGKILKCECNGWLKSDGRTDYVKLFLPIAIRLREDKTKANTFEDVFGD   480

481 FHEVTGLGSGSSGHHHHHH*                                          499
```

T4 DNA Ligase CH E440A DNA

SEQ ID NO: 37

```
  1 ATGATTCTTAAAATTCTGAACGAAATAGCATCTATTGGTTCAACTAAACAGAAGCAAGCA    60

61 ATTCTTGAAAAGAATAAAGATAATGAATTGCTTAAACGAGTATATCGTCTGACTTATTCT   120

121 CGTGGGTTACAGTATTATATCAAGAAATGGCCTAAACCTGGTATTGCTACCCAGAGTTTT   180

181 GGAATGTTGACTCTTACCGATATGCTTGACTTCATTGAATTCACATTAGCTACTCGGAAA   240

241 TTGACTGGAAATGCAGCAATTGAGGAATTAACTGGATATATCACCGATGGTAAAAAGAT   300

301 GATGTTGAAGTTTTGCGTCGAGTGATGATGCGAGACCTTGAATGTGGTGCTTCAGTATCT   360

361 ATTGCAAACAAAGTTTGGCCAGGTTTAATTCCTGAACAACCTCAAATGCTCGCAAGTTCT   420

421 TATGATGAAAAGGCATTAATAAGAATATCAAATTTCCAGCCTTTGCTCAGTTAAAAGCT   480
```

-continued

```
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTGATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAAATTATTATATTGGAAAAATTCTAGAGTGCGCA 1320
1321 TGCAACGGTTGGTTAAAATCTGATGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH E440A Protein

SEQ ID NO: 38

```
  1 MILKILNEIASIGSTKQKQAILEKNKDNELLKRVYRLTYSRGLQYYIKKWPKPGIATQSF   60
 61 GMLTLTDMLDFIEFTLATRKLTGNAAIEELTGYITDGKKDDVEVLRRVMMRDLECGASVS  120
121 IANKVWPGLIPEQPQMLASSYDEKGINKNIKFPAFAQLKADGARCFAEVRGDELDDVRLL  180
181 SRAGNEYLGLDLLKEELIKMTAEARQIHPEGVLIDGELVYHEQVKKEPEGLDFLFDAYPE  240
241 NSKAKEFAEVAESRTASNGIANKSLKGTISEKEAQCMKFQVWDYVPLVEIYSLPAFRLKY  300
301 DVRFSKLEQMTSGYDKVILIENQVVNNLDEAKVIYKKYIDQGLEGIILKNIDGLWENARS  360
361 KNLYKFKEVIDVDLKIVGIYPHRKDPTKAGGFILESECGKIKVNAGSLKDKAGVKSHEL   420
421 DRTRIMENQNYYIGKILECACNGWLKSDGRTDYVKLFLPIAIRLREDKTKANTFEDVFGD  480
481 FHEVTGLGSGSSGHHHHHH*                                         499
```

T4 DNA Ligase CH E440H DNA

SEQ ID NO: 39

```
  1 ATGATTCTTAAAATTCTGAACGAAATAGCATCTATTGGTTCAACTAAACAGAAGCAAGCA   60
 61 ATTCTTGAAAAGAATAAAGATAATGAATTGCTTAAACGAGTATATCGTCTGACTTATTCT  120
121 CGTGGGTTACAGTATTATATCAAGAAATGGCCTAAACCTGGTATTGCTACCCAGAGTTTT  180
181 GGAATGTTGACTCTTACCGATATGCTTGACTTCATTGAATTCACATTAGCTACTCGGAAA  240
241 TTGACTGGAAATGCAGCAATTGAGGAATTAACTGGATATATCACCGATGGTAAAAAAGAT  300
301 GATGTTGAAGTTTTGCGTCGAGTGATGATGCGAGACCTTGAATGTGGTGCTTCAGTATCT  360
361 ATTGCAAACAAAGTTTGGCCAGGTTTAATTCCTGAACAACCTCAAATGCTCGCAAGTTCT  420
421 TATGATGAAAAAGGCATTAATAAGAATATCAAATTTCCAGCCTTTGCTCAGTTAAAAGCT  480
481 GATGGAGCTCGGTGTTTTGCTGAAGTTAGAGGTGATGAATTAGATGATGTTCGTCTTTTA  540
541 TCACGAGCTGGTAATGAATATCTAGGATTAGATCTTCTTAAGGAAGAGTTAATTAAAATG  600
601 ACCGCTGAAGCCCGCCAGATTCATCCAGAAGGTGTGTTGATTGATGGCGAATTGGTATAC  660
661 CATGAGCAAGTTAAAAAGGAGCCAGAAGGCCTAGATTTTCTTTTTGATGCTTATCCTGAA  720
721 AACAGTAAAGCTAAAGAATTCGCCGAAGTAGCTGAATCACGTACTGCTTCTAATGGAATC  780
```

-continued

```
 781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTCTAAACTAGAACAAATGACATCTGGATATGATAAAGTAATTTTAATT   960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCCAT 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH E440H Protein

SEQ ID NO: 40

```
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIDVDLKIVGIYPHRKDPTKAGGFILESECGKIKVNAGSGLKDKAGVKSHEL  420

421 DRTRIMENQNYYIGKILECHCNGWLKSDGRTDYVKLFLPIAIRLREDKTKANTFEDVFGD  480

481 FHEVTGLGSGSSGHHHHHH*                                          499
```

T4 DNA Ligase CH E440K DNA

SEQ ID NO: 41

```
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAGGCATTAATAAGAATATCAAATTTCCAGCCTTTGCTCAGTTAAAAGCT   480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020
```

-continued

```
1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCAAA 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH E440K Protein
SEQ ID NO: 42

```
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360

361 KNLYKFKEVIDVDLKIVGIYPHRKDPTKAGGFILESECGKIKVNAGSGLKDKAGVKSHEL  420

421 DRTRIMENQNYYIGKILECKCNGWLKSDGRTDYVKLFLPIAIRLREDKTKANTFEDVFGD  480

481 FHEVTGLGSGSSGHHHHHH*                                          499
```

T4 DNA Ligase CH E440N DNA
SEQ ID NO: 43

```
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCAAC 1320
```

-continued

```
1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

T4 DNA Ligase CH E440N Protein

SEQ ID NO: 44
```
  1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180

181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIDVDLKIVGIYPHRKDPTKAGGFILESECGKIKVNAGSGLKDKAGVKSHEL   420

421 DRTRIMENQNYYIGKILECNCNGWLKSDGRTDYVKLFLPIAIRLREDKTKANTFEDVFGD   480

481 FHEVTGLGSGSSGHHHHHH*                                          499
```

T4 DNA Ligase CH E440R DNA

SEQ ID NO: 45
```
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCCGT 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500
```

-continued

```
T4 DNA Ligase CH E440R Protein
                                                  SEQ ID NO: 46
   1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180

181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIDVDLKIVGIYPHRKDPTKAGGFILESECGKIKVNAGSGLKDKAGVKSHEL   420

421 DRTRIMENQNYYIGKILECRCNGWLKSDGRTDYVKLFLPIAIRLREDKTKANTFEDVFGD   480

481 FHEVTGLGSGSSGHHHHHH*                                          499

T4 DNA Ligase CH E440S DNA
                                                  SEQ ID NO: 47
   1 ATGATTCTTAAAATTCTGAACGAAATAGCATCTATTGGTTCAACTAAACAGAAGCAAGCA    60

61 ATTCTTGAAAAGAATAAAGATAATGAATTGCTTAAACGAGTATATCGTCTGACTTATTCT   120

121 CGTGGGTTACAGTATTATATCAAGAAATGGCCTAAACCTGGTATTGCTACCCAGAGTTTT   180

181 GGAATGTTGACTCTTACCGATATGCTTGACTTCATTGAATTCACATTAGCTACTCGGAAA   240

241 TTGACTGGAAATGCAGCAATTGAGGAATTAACTGGATATATCACCGATGGTAAAAAAGAT   300

301 GATGTTGAAGTTTTGCGTCGAGTGATGATGCGAGACCTTGAATGTGGTGCTTCAGTATCT   360

361 ATTGCAAACAAAGTTTGGCCAGGTTTAATTCCTGAACAACCTCAAATGCTCGCAAGTTCT   420

421 TATGATGAAAAAGGCATTAATAAGAATATCAAATTTCCAGCCTTTGCTCAGTTAAAAGCT   480

481 GATGGAGCTCGGTGTTTTGCTGAAGTTAGAGGTGATGAATTAGATGATGTTCGTCTTTTA   540

541 TCACGAGCTGGTAATGAATATCTAGGATTAGATCTTCTTAAGGAAGAGTTAATTAAAATG   600

601 ACCGCTGAAGCCCGCCAGATTCATCCAGAAGGTGTGTTGATTGATGGCGAATTGGTATAC   660

661 CATGAGCAAGTTAAAAAGGAGCCAGAAGGCCTAGATTTTCTTTTTGATGCTTATCCTGAA   720

721 AACAGTAAAGCTAAAGAATTCGCCGAAGTAGCTGAATCACGTACTGCTTCTAATGGAATC   780

781 GCCAATAAATCTTTAAAGGGAACCATTTCTGAAAAAGAAGCACAATGCATGAAGTTTCAG   840

841 GTCTGGGATTATGTCCCGTTGGTAGAAATATACAGTCTTCCTGCATTTCGTTTGAAATAT   900

901 GATGTACGTTTTTCTAAACTAGAACAAATGACATCTGGATATGATAAAGTAATTTTAATT   960

961 GAAAACCAGGTAGTAAATAACCTAGATGAAGCTAAGGTAATTTATAAAAAGTATATTGAC  1020

1021 CAAGGTCTTGAAGGTATTATTCTCAAAAATATCGATGGATTATGGGAAAATGCTCGTTCA  1080

1081 AAAAATCTTTATAAATTTAAAGAAGTAATTGATGTTGATTTAAAAATTGTAGGAATTTAT  1140

1141 CCTCACCGTAAAGACCCTACTAAAGCGGGTGGATTTATTCTTGAGTCAGAGTGTGGAAAA  1200

1201 ATTAAGGTAAATGCTGGTTCAGGCTTAAAAGATAAAGCCGGTGTAAAATCGCATGAACTT  1260

1261 GACCGTACTCGCATTATGGAAAACCAAAATTATTATATTGGAAAAATTCTAGAGTGCTCT  1320

1321 TGCAACGGTTGGTTAAAATCTGATGGCCGCACTGATTACGTTAAATTATTTCTTCCGATT  1380

1381 GCGATTCGTTTACGTGAAGATAAAACTAAAGCTAATACATTCGAAGATGTATTTGGTGAT  1440

1441 TTTCATGAGGTAACTGGTCTAGGTTCTGGCAGTTCAGGTCATCACCACCATCATCACTAA  1500

T4 DNA Ligase CH E440S Protein
                                                  SEQ ID NO: 48
   1 MILKILNEIASIGSTKQKQAILEKNKDNELLKRVYRLTYSRGLQYYIKKWPKPGIATQSF    60

61 GMLTLTDMLDFIEFTLATRKLTGNAAIEELTGYITDGKKDDVEVLRRVMMRDLECGASVS   120

121 IANKVWPGLIPEQPQMLASSYDEKGINKNIKFPAFAQLKADGARCFAEVRGDELDDVRLL   180
```

```
181 SRAGNEYLGLDLLKEELIKMTAEARQIHPEGVLIDGELVYHEQVKKEPEGLDFLFDAYPE   240

241 NSKAKEFAEVAESRTASNGIANKSLKGTISEKEAQCMKFQVWDYVPLVEIYSLPAFRLKY   300

301 DVRFSKLEQMTSGYDKVILIENQVVNNLDEAKVIYKKYIDQGLEGIILKNIDGLWENARS   360

361 KNLYKFKEVIDVDLKIVGIYPHRKDPTKAGGFILESECGKIKVNAGSGLKDKAGVKSHEL   420

421 DRTRIMENQNYYIGKILECSCNGWLKSDGRTDYVKLFLPIAIRLREDKTKANTFEDVFGD   480

481 FHEVTGLGSGSSGHHHHHH*                                          499

T4 DNA Ligase CH E440W DNA
                                                  SEQ ID NO: 49
  1 ATGATTCTTAAAATTCTGAACGAAATAGCATCTATTGGTTCAACTAAACAGAAGCAAGCA   60

61 ATTCTTGAAAAGAATAAAGATAATGAATTGCTTAAACGAGTATATCGTCTGACTTATTCT  120

121 CGTGGGTTACAGTATTATATCAAGAAATGGCCTAAACCTGGTATTGCTACCCAGAGTTTT  180

181 GGAATGTTGACTCTTACCGATATGCTTGACTTCATTGAATTCACATTAGCTACTCGGAAA  240

241 TTGACTGGAAATGCAGCAATTGAGGAATTAACTGGATATATCACCGATGGTAAAAAAGAT  300

301 GATGTTGAAGTTTTGCGTCGAGTGATGATGCGAGACCTTGAATGTGGTGCTTCAGTATCT  360

361 ATTGCAAACAAAGTTTGGCCAGGTTTAATTCCTGAACAACCTCAAATGCTCGCAAGTTCT  420

421 TATGATGAAAAGGCATTAATAAGAATATCAAATTTCCAGCCTTTGCTCAGTTAAAAGCT  480

481 GATGGAGCTCGGTGTTTTGCTGAAGTTAGAGGTGATGAATTAGATGATGTTCGTCTTTTA  540

541 TCACGAGCTGGTAATGAATATCTAGGATTAGATCTTCTTAAGGAAGAGTTAATTAAAATG  600

601 ACCGCTGAAGCCCGCCAGATTCATCCAGAAGGTGTGTTGATTGATGGCGAATTGGTATAC  660

661 CATGAGCAAGTTAAAAAGGAGCCAGAAGGCCTAGATTTTCTTTTTGATGCTTATCCTGAA  720

721 AACAGTAAAGCTAAAGAATTCGCCGAAGTAGCTGAATCACGTACTGCTTCTAATGGAATC  780

781 GCCAATAAATCTTTAAAGGGAACCATTTCTGAAAAAGAAGCACAATGCATGAAGTTTCAG  840

841 GTCTGGGATTATGTCCCGTTGGTAGAAATATACAGTCTTCCTGCATTTCGTTTGAAATAT  900

901 GATGTACGTTTTTCTAAACTAGAACAAATGACATCTGGATATGATAAAGTAATTTTAATT  960

961 GAAAACCAGGTAGTAAATAACCTAGATGAAGCTAAGGTAATTTATAAAAAGTATATTGAC 1020

1021 CAAGGTCTTGAAGGTATTATTCTCAAAAATATCGATGGATTATGGGAAAATGCTCGTTCA 1080

1081 AAAAATCTTTATAAATTTAAAGAAGTAATTGATGTTGATTTAAAAATTGTAGGAATTTAT 1140

1141 CCTCACCGTAAAGACCCTACTAAAGCGGGTGGATTTATTCTTGAGTCAGAGTGTGGAAAA 1200

1201 ATTAAGGTAAATGCTGGTTCAGGCTTAAAAGATAAAGCCGGTGTAAAATCGCATGAACTT 1260

1261 GACCGTACTCGCATTATGGAAAACCAAAATTATTATATTGGAAAAATTCTAGAGTGCTGG 1320

1321 TGCAACGGTTGGTTAAAATCTGATGGCCGCACTGATTACGTTAAATTATTTCTTCCGATT 1380

1381 GCGATTCGTTTACGTGAAGATAAAACTAAAGCTAATACATTCGAAGATGTATTTGGTGAT 1440

1441 TTTCATGAGGTAACTGGTCTAGGTTCTGGCAGTTCAGGTCATCACCACCATCATCACTAA 1500

T4 DNA Ligase CH E440W Protein
                                                  SEQ ID NO: 50
  1 MILKILNEIASIGSTKQKQAILEKNKDNELLKRVYRLTYSRGLQYYIKKWPKPGIATQSF   60

61 GMLTLTDMLDFIEFTLATRKLTGNAAIEELTGYITDGKKDDVEVLRRVMMRDLECGASVS  120

121 IANKVWPGLIPEQPQMLASSYDEKGINKNIKFPAFAQLKADGARCFAEVRGDELDDVRLL  180

181 SRAGNEYLGLDLLKEELIKMTAEARQIHPEGVLIDGELVYHEQVKKEPEGLDFLFDAYPE  240

241 NSKAKEFAEVAESRTASNGIANKSLKGTISEKEAQCMKFQVWDYVPLVEIYSLPAFRLKY  300

301 DVRFSKLEQMTSGYDKVILIENQVVNNLDEAKVIYKKYIDQGLEGIILKNIDGLWENARS  360
```

```
361 KNLYKFKEVIDVDLKIVGIYPHRKDPTKAGGFILESECGKIKVNAGSGLKDKAGVKSHEL  420
421 DRTRIMENQNYYIGKILECWCNGWLKSDGRTDYVKLFLPIAIRLREDKTKANTFEDVFGD  480
481 FHEVTGLGSGSSGHHHHHH*                                         499
```

T4 DNA Ligase CH D448R DNA

SEQ ID NO: 51

```
   1 ATGATTCTTAAAATTCTGAACGAAATAGCATCTATTGGTTCAACTAAACAGAAGCAAGCA   60
  61 ATTCTTGAAAAGAATAAAGATAATGAATTGCTTAAACGAGTATATCGTCTGACTTATTCT  120
 121 CGTGGGTTACAGTATTATATCAAGAAATGGCCTAAACCTGGTATTGCTACCCAGAGTTTT  180
 181 GGAATGTTGACTCTTACCGATATGCTTGACTTCATTGAATTCACATTAGCTACTCGGAAA  240
 241 TTGACTGGAAATGCAGCAATTGAGGAATTAACTGGATATATCACCGATGGTAAAAAGAT   300
 301 GATGTTGAAGTTTTGCGTCGAGTGATGATGCGAGACCTTGAATGTGGTGCTTCAGTATCT  360
 361 ATTGCAAACAAAGTTTGGCCAGGTTTAATTCCTGAACAACCTCAAATGCTCGCAAGTTCT  420
 421 TATGATGAAAAAGGCATTAATAAGAATATCAAATTTCCAGCCTTTGCTCAGTTAAAAGCT  480
 481 GATGGAGCTCGGTGTTTTGCTGAAGTTAGAGGTGATGAATTAGATGATGTTCGTCTTTTA  540
 541 TCACGAGCTGGTAATGAATATCTAGGATTAGATCTTCTTAAGGAAGAGTTAATTAAAATG  600
 601 ACCGCTGAAGCCCGCCAGATTCATCCAGAAGGTGTGTTGATTGATGGCGAATTGGTATAC  660
 661 CATGAGCAAGTTAAAAAGGAGCCAGAAGGCCTAGATTTTCTTTTTGATGCTTATCCTGAA  720
 721 AACAGTAAAGCTAAAGAATTCGCCGAAGTAGCTGAATCACGTACTGCTTCTAATGGAATC  780
 781 GCCAATAAATCTTTAAAGGGAACCATTTCTGAAAAAGAAGCACAATGCATGAAGTTTCAG  840
 841 GTCTGGGATTATGTCCCGTTGGTAGAAATATACAGTCTTCCTGCATTTCGTTTGAAATAT  900
 901 GATGTACGTTTTTCTAAACTAGAACAAATGACATCTGGATATGATAAAGTAATTTTAATT  960
 961 GAAAACCAGGTAGTAAATAACCTAGATGAAGCTAAGGTAATTTATAAAAAGTATATTGAC 1020
1021 CAAGGTCTTGAAGGTATTATTCTCAAAAATATCGATGGATTATGGGAAAATGCTCGTTCA 1080
1081 AAAAATCTTTATAAATTTAAAGAAGTAATTGATGTTGATTTAAAAATTGTAGGAATTTAT 1140
1141 CCTCACCGTAAAGACCCTACTAAAGCGGGTGGATTTATTCTTGAGTCAGAGTGTGGAAAA 1200
1201 ATTAAGGTAAATGCTGGTTCAGGCTTAAAAGATAAAGCCGGTGTAAAATCGCATGAACTT 1260
1261 GACCGTACTCGCATTATGGAAAACCAAAATTATTATATTGGAAAAATTCTAGAGTGCGAA 1320
1321 TGCAACGGTTGGTTAAAATCTCGTGGCCGCACTGATTACGTTAAATTATTTCTTCCGATT 1380
1381 GCGATTCGTTTACGTGAAGATAAAACTAAAGCTAATACATTCGAAGATGTATTTGGTGAT 1440
1441 TTTCATGAGGTAACTGGTCTAGGTTCTGGCAGTTCAGGTCATCACCACCATCATCACTAA 1500
```

T4 DNA Ligase CH D448R Protein

SEQ ID NO: 52

```
   1 MILKILNEIASIGSTKQKQAILEKNKDNELLKRVYRLTYSRGLQYYIKKWPKPGIATQSF   60
  61 GMLTLTDMLDFIEFTLATRKLTGNAAIEELTGYITDGKKDDVEVLRRVMMRDLECGASVS  120
 121 IANKVWPGLIPEQPQMLASSYDEKGINKNIKFPAFAQLKADGARCFAEVRGDELDDVRLL  180
 181 SRAGNEYLGLDLLKEELIKMTAEARQIHPEGVLIDGELVYHEQVKKEPEGLDFLFDAYPE  240
 241 NSKAKEFAEVAESRTASNGIANKSLKGTISEKEAQCMKFQVWDYVPLVEIYSLPAFRLKY  300
 301 DVRFSKLEQMTSGYDKVILIENQVVNNLDEAKVIYKKYIDQGLEGIILKNIDGLWENARS  360
 361 KNLYKFKEVIDVDLKIVGIYPHRKDPTKAGGFILESECGKIKVNAGSGLKDKAGVKSHEL  420
 421 DRTRIMENQNYYIGKILECECNGWLKSRGRTDYVKLFLPIAIRLREDKTKANTFEDVFGD  480
 481 FHEVTGLGSGSSGHHHHHH*                                         499
```

What is claimed is:

1. A mutant T4 DNA ligase having 95% sequence identity to SEQ ID NO:4 and comprising the amino acid substitution E88K.

2. A mutant T4 DNA ligase having 99% sequence identity to SEQ ID NO:4 and comprising the amino acid substitution E88K.

3. A process of conducting polynucleotide ligation between two different polynucleotides or by ligating the 5' and 3' end of a single polynucleotide to generate a circular polynucleotide, wherein the polynucleotides have blunt ends or cohesive ends, comprising: providing a ligation mixture including the polynucleotide(s) to be ligated and the mutant T4 DNA ligase of claim 1 with a concentration of salt in the ligation mixture of greater than or equal to 250 mM; and placing said ligation mixture at a temperature wherein ligation takes place.

4. The process of claim 3 wherein the salt is NaCl.

5. The process of claim 3 wherein the ligation reaction mixture includes Tris-HCl, $MgCl_2$, ATP, dithiothreitol and water.

6. A process of conducting polynucleotide ligation between two different polynucleotides or by ligating the 5' and 3' end of a single polynucleotide to generate a circular polynucleotide, wherein the polynucleotides have blunt ends or cohesive ends, comprising: providing a ligation mixture including the polynucleotide(s) to be ligated and the mutant T4 DNA ligase of claim 2 with a concentration of salt in the ligation mixture of greater than or equal to 250 mM; and placing said ligation mixture at a temperature wherein ligation takes place.

7. The process of claim 6 wherein the salt is NaCl.

8. The process of claim 6 wherein the ligation reaction mixture includes Tris-HCl, $MgCl_2$, ATP, dithiothreitol and water.

9. The mutant T4 DNA ligase of claim 1, having the amino acid sequence of SEQ ID NO: 4, but not including the 6-membered histidine tag at its C-terminus and the seven immediately preceding Glycine and Serine amino acids.

* * * * *

SEQUENCE LISTING

<160> NUMBER OF SEQ ID NOS: 54

<210> SEQ ID NO 1
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttttgatgc ttatcctgaa     720
aacagtaaag ctaagaatt cgccgaagta gctgaatcac gtactgcttc taatggaatc     780
gccaataaat cttttaaaggg aaccatttct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aatttttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat    1440
tttcatgagg taactggtct aggttctggc agttcaggtc atcaccacca tcatcactaa    1500
```

<210> SEQ ID NO 2
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Ile Leu Lys Ile Leu Asn Glu Ile Ala Ser Ile Gly Ser Thr Lys
 1               5                  10                  15

Gln Lys Gln Ala Ile Leu Glu Lys Asn Lys Asp Asn Glu Leu Leu Lys
            20                  25                  30
```

```
Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
            210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445
```

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 3
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | | |
|---|---|---|
| atgattctta aaattctgaa cgaaatagca tctattggtt caactaaaca gaagcaagca | 60 |
| attcttgaaa agaataaaga taatgaattg cttaaacgag tatatcgtct gacttattct | 120 |
| cgtgggttac agtattatat caagaaatgg cctaaacctg gtattgctac ccagagtttt | 180 |
| ggaatgttga ctcttaccga tatgcttgac ttcattgaat tcacattagc tactcggaaa | 240 |
| ttgactggaa atgcagcaat taagaatta actggatata tcaccgatgg taaaaaagat | 300 |
| gatgttgaag ttttgcgtcg agtgatgatg cgagaccttg aatgtggtgc ttcagtatct | 360 |
| attgcaaaca agtttggcc aggtttaatt cctgaacaac ctcaaatgct cgcaagttct | 420 |
| tatgatgaaa aaggcattaa taagaatatc aaatttccag cctttgctca gttaaaagct | 480 |
| gatggagctc ggtgttttgc tgaagttaga ggtgatgaat tagatgatgt tcgtctttta | 540 |
| tcacgagctg gtaatgaata tctaggatta gatcttctta aggaagagtt aattaaaatg | 600 |
| accgctgaag cccgccagat tcatccagaa ggtgtgttga ttgatggcga attggtatac | 660 |
| catgagcaag ttaaaaagga gccagaaggc ctagattttc tttttgatgc ttatcctgaa | 720 |
| aacagtaaag ctaagaatt cgccgaagta gctgaatcac gtactgcttc taatggaatc | 780 |
| gccaataaat ctttaaaggg aaccatttct gaaaaagaag cacaatgcat gaagtttcag | 840 |
| gtctgggatt atgtcccgtt ggtagaaata tacagtcttc ctgcatttcg tttgaaatat | 900 |
| gatgtacgtt tttctaaact agaacaaatg acatctggat atgataaagt aatttaatt | 960 |
| gaaaaccagg tagtaaataa cctagatgaa gctaaggtaa tttataaaaa gtatattgac | 1020 |
| caaggtcttg aaggtattat tctcaaaaat atcgatggat tatgggaaaa tgctcgttca | 1080 |
| aaaaatcttt ataaatttaa agaagtaatt gatgttgatt taaaaattgt aggaatttat | 1140 |
| cctcaccgta aagaccctac taaagcgggt ggatttattc ttgagtcaga gtgtggaaaa | 1200 |
| attaaggtaa atgctggttc aggcttaaaa gataaagccg gtgtaaaatc gcatgaactt | 1260 |
| gaccgtactc gcattatgga aaaccaaaat tattatattg gaaaaattct agagtgcgaa | 1320 |
| tgcaacggtt ggttaaaatc tgatggccgc actgattacg ttaaattatt tcttccgatt | 1380 |
| gcgattcgtt tacgtgaaga taaaactaaa gctaatacat tcgaagatgt atttggtgat | 1440 |
| tttcatgagg taactggtct aggttctggc agttcaggtc atcaccacca tcatcactaa | 1500 |

<210> SEQ ID NO 4
<211> LENGTH: 499
<212> TYPE: PRT
<213> ORGANISM: Artificial Sequence
<220> FEATURE:
<223> OTHER INFORMATION: Description of Artificial Sequence: Synthetic

```
                            polypeptide

<400> SEQUENCE: 4

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Lys Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400
```

```
Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His
```

<210> SEQ ID NO 5
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atgattctta aaattctgaa cgaaatagca tctattggtt caactaaaca gaagcaagca    60
attcttgaaa agaataaaga taatgaattg cttaaacgag tatatcgtct gacttattct   120
cgtgggttac agtattatat caagaaatgg cctaaacctg gtattgctac ccagagtttt   180
ggaatgttga ctcttaccga tatgcttgac ttcattgaat tcacattagc tactcggaaa   240
ttgactggaa atgcagcaat tgaggaatta actggatata tcaccgatgg taaaaaagat   300
gatgttgaag ttttgcgtcg agtgatgatg cgagaccttg aatgtggtgc ttcagtatct   360
attgcaaaca agtttggcc aggtttaatt cctaaacaac ctcaaatgct cgcaagttct   420
tatgatgaaa aaggcattaa taagaatatc aaatttccag cctttgctca gttaaaagct   480
gatggagctc ggtgttttgc tgaagttaga ggtgatgaat tagatgatgt tcgtctttta   540
tcacgagctg gtaatgaata tctaggatta gatcttctta aggaagagtt aattaaaatg   600
accgctgaag cccgccagat tcatccagaa ggtgtgttga ttgatggcga attggtatac   660
catgagcaag ttaaaaagga gccagaaggc ctagattttc ttttttgatgc ttatcctgaa   720
aacagtaaag ctaaagaatt cgccgaagta gctgaatcac gtactgcttc taatggaatc   780
gccaataaat cttaaagggg aaccatttct gaaaaagaag cacaatgcat gaagtttcag   840
gtctgggatt atgtcccgtt ggtagaaata tacagtcttc ctgcatttcg tttgaaatat   900
gatgtacgtt tttctaaact agaacaaatg acatctggat atgataaagt aattttaatt   960
gaaaaccagg tagtaaataa cctagatgaa gctaaggtaa tttataaaaa gtatattgac  1020
caaggtcttg aaggtattat tctcaaaaat atcgatggat tatgggaaaa tgctcgttca  1080
aaaaatcttt ataaatttaa agaagtaatt gatgttgatt taaaaattgt aggaatttat  1140
cctcaccgta aagaccctac taaagcgggt ggatttattc ttgagtcaga gtgtggaaaa  1200
attaaggtaa atgctggttc aggcttaaaa gataaagccg gtgtaaaatc gcatgaactt  1260
gaccgtactc gcattatgga aaaccaaaat tattatattg aaaaattct agagtgcgaa  1320
tgcaacggtt ggttaaaatc tgatggccgc actgattacg ttaaattatt tcttccgatt  1380
gcgattcgtt tacgtgaaga taaaactaaa gctaatacat cgaagatgt atttggtgat  1440
```

-continued tttcatgagg taactggtct aggttctggc agttcaggtc atcaccacca tcatcactaa    1500

<210> SEQ ID NO 6
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Lys Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350
```

-continued

```
Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
            485                 490                 495

His His His
```

<210> SEQ ID NO 7
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtcttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
cataaacaag ttaaaaagga gccagaaggc ctagattttc ttttgatgc ttatcctgaa      720
aacagtaaag ctaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt ttctaaact agaacaaatg acatctggat atgataagt aattttaatt     960
gaaaaccagg tagtaaataa cctagatgaa gctaaggtaa tttataaaaa gtatattgac    1020
caaggtcttg aagtattat tctcaaaaat atcgatggat atgggaaaa tgctcgttca    1080
aaaaatcttt ataatttaa agaagtaatt gatgttgatt taaaaattgt aggaattat    1140
cctcaccgta aagaccctac taaagcgggt ggatttattc ttgagtcaga gtgtggaaaa    1200
```

-continued

```
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 8
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Lys Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300
```

| | | | | | | | | | | | | |
|---|---|---|---|---|---|---|---|---|---|---|---|---|
|Ser|Lys|Leu|Glu|Gln|Met|Thr|Ser|Gly|Tyr|Asp|Lys|Val|Ile|Leu|Ile|
|305| | | |310| | | |315| | | |320|

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
            485                 490                 495

His His His

<210> SEQ ID NO 9
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtcttta     540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
gccaataaat ctttaaaggg aaccattcct gaaaagaag cacaatgcat gaagtttcag     840
gtctgggatt atgtccctt ggtagaaata tacagtcttc ctgcatttcg ttgaaatat     900

```
gatgtacgtt tttctgaact agaacaaatg acatctggat atgataaagt aattttaatt      960
gaaaaccagg tagtaaataa cctagatgaa gctaaggtaa tttataaaaa gtatattgac     1020
caaggtcttg aaggtattat tctcaaaaat atcgatggat tatgggaaaa tgctcgttca     1080
aaaaatcttt ataaatttaa agaagtaatt gatgttgatt taaaaattgt aggaatttat     1140
cctcaccgta aagaccctac taaagcgggt ggatttattc ttgagtcaga gtgtggaaaa     1200
attaaggtaa atgctggttc aggcttaaaa gataaagccg gtgtaaaatc gcatgaactt     1260
gaccgtactc gcattatgga aaaccaaaat tattatattg gaaaaattct agagtgcgaa     1320
tgcaacggtt ggttaaaatc tgatggccgc actgattacg ttaaattatt tcttccgatt     1380
gcgattcgtt tacgtgaaga taaaactaaa gctaatacat tcgaagatgt atttggtgat     1440
tttcatgagg taactggtct aggttctggc agttcaggtc atcaccacca tcatcactaa     1500
```

<210> SEQ ID NO 10
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255
```

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Glu Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 11
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac tcaaatgct cgcaagttct     420 tatgatgaaa aaggcattaa taagaatatc aaatttccag cctttgctca gttaaaagct     480
gatggagctc ggtgttttgc tgaagttaga ggtgatgaat tagatgatgt tcgtcttta     540 tcacgagctg gtaatgaata tctaggatta gatcttctta aggaagagtt aattaaaatg     600
accgctgaag cccgccagat tcatccagaa ggtgtgttga ttgatggcga attggtatac     660

```
catgagcaag ttaaaaagga gccagaaggc ctagattttc tttttgatgc ttatcctgaa    720
aacagtaaag ctaagaatt cgccgaagta gctgaatcac gtactgcttc taatggaatc    780
gccaataaat ctttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattcgt   1020
caaggtcttg aaggtattat tctcaaaaat atcgatggat tatgggaaaa tgctcgttca   1080
aaaaatcttt ataaatttaa agaagtaatt gatgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 12
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205
```

```
Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Arg Gln Gly Leu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
370                 375                 380

Asp Pro Thr Lys Ala Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His
                485                 490                 495

His His His

<210> SEQ ID NO 13
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
```

```
attgcaaaca aagtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaagaatt cgccgaagta gctgaatcac gtactgcttc taatggaatc    780
gccaataaat ctttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aagtattat tctcaaaaat atcgatggat tatgggaaaa tgctcgttca   1080
aaaaatcttt atgaatttaa agaagtaatt gatgttgatt taaaaattgt aggaattat   1140 cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaccaaaat tattatattg gaaaaattct agagtgcgaa   1320
tgcaacggtt ggtaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 14
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160
```

```
Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Glu Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 15
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgattctta aaattctgaa cgaaatagca tctattggtt caactaaaca gaagcaagca      60
attcttgaaa agaataaaga taatgaattg cttaaacgag tatatcgtct gacttattct    120
```

```
cgtgggttac agtattatat caagaaatgg cctaaacctg gtattgctac ccagagtttt    180
ggaatgttga ctcttaccga tatgcttgac ttcattgaat tcacattagc tactcggaaa    240
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca agtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540 tcacagagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat ctttaaaggg aaccatttct gaaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt gcagttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 16
<211> LENGTH: 499
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 16

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Arg Asp
            100                 105                 110
```

Leu Glu Cys Gly Ala Ser Val Ser Ile Ala Asn Lys Val Trp Pro Gly
115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Ala Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 17
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | | | | | |
|---|---|---|---|---|---|
| atgattctta | aaattctgaa | cgaaatagca | tctattggtt | caactaaaca | gaagcaagca | 60 |
| attcttgaaa | agaataaaga | taatgaattg | cttaaacgag | tatatcgtct | gacttattct | 120 |
| cgtgggttac | agtattatat | caagaaatgg | cctaaacctg | gtattgctac | ccagagtttt | 180 |
| ggaatgttga | ctcttaccga | tatgcttgac | ttcattgaat | tcacattagc | tactcggaaa | 240 |
| ttgactggaa | atgcagcaat | tgaggaatta | actggatata | tcaccgatgg | taaaaaagat | 300 |
| gatgttgaag | ttttgcgtcg | agtgatgatg | cgagaccttg | aatgtggtgc | ttcagtatct | 360 |
| attgcaaaca | agtttggcc | aggtttaatt | cctgaacaac | tcaaatgct | cgcaagttct | 420 |
| tatgatgaaa | aaggcattaa | taagaatatc | aaatttccag | cctttgctca | gttaaaagct | 480 |
| gatggagctc | ggtgttttgc | tgaagttaga | ggtgatgaat | tagatgatgt | tcgtctttta | 540 |
| tcacgagctg | gtaatgaata | tctaggatta | gatcttctta | aggaagagtt | aattaaaatg | 600 |
| accgctgaag | cccgccagat | tcatccagaa | ggtgtgttga | ttgatggcga | attggtatac | 660 |
| catgagcaag | ttaaaaagga | gccagaaggc | ctagattttc | tttttgatgc | ttatcctgaa | 720 |
| aacagtaaag | ctaaagaatt | cgccgaagta | gctgaatcac | gtactgcttc | taatggaatc | 780 |
| gccaataaat | ctttaaaggg | aaccatttct | gaaaagaag | cacaatgcat | gaagtttcag | 840 |
| gtctgggatt | atgtcccgtt | ggtagaaata | tacagtcttc | ctgcatttcg | tttgaaatat | 900 |
| gatgtacgtt | tttctaaact | agaacaaatg | acatctggat | atgataaagt | aattttaatt | 960 |
| gaaaaccagg | tagtaaataa | cctagatgaa | gctaaggtaa | tttataaaaa | gtatattgac | 1020 |
| caaggtcttg | aaggtattat | tctcaaaaat | atcgatggat | tatgggaaaa | tgctcgttca | 1080 |
| aaaaatcttt | ataaatttaa | agaagtaatt | ggtgttgatt | taaaaattgt | aggaatttat | 1140 |
| cctcaccgta | aagaccctac | taaagcgggt | ggatttattc | ttgagtcaga | gtgtggaaaa | 1200 |
| attaaggtaa | atgctggttc | aggcttaaaa | gataaagccg | gtgtaaaatc | gcatgaactt | 1260 |
| gaccgtactc | gcattatgga | aaaccaaaat | tattatattg | gaaaaattct | agagtgcgaa | 1320 |
| tgcaacggtt | ggttaaaatc | tgatggccgc | actgattacg | ttaaattatt | tcttccgatt | 1380 |
| gcgattcgtt | tacgtgaaga | taaaactaaa | gctaatacat | tcgaagatgt | atttggtgat | 1440 |
| tttcatgagg | taactggtct | aggttctggc | agttcaggtc | atcaccacca | tcatcactaa | 1500 |

<210> SEQ ID NO 18
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60
```

```
Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                 85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Gly Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
```

His His His

<210> SEQ ID NO 19
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtcttta      540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat ctttaaaggg aaccatttct gaaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt catgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat     1440
tttcatgagg taactggtct aggttctggc agttcaggtc atcaccacca tcatcactaa    1500
```

<210> SEQ ID NO 20
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Ile Leu Lys Ile Leu Asn Glu Ile Ala Ser Ile Gly Ser Thr Lys
1               5                   10                  15
```

-continued

```
Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
 50                  55                  60

Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
                115                 120                 125

Leu Ile Pro Glu Gln Pro Gln Met Leu Ala Ser Ser Tyr Asp Glu Lys
                130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
 210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
 290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile His Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
```

435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 21
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaattc gccgaagta gctgaatcac gtactgcttc taatggaatc     780
gccaataaat cttttaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt attgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcgaa    1320
tgcaacggtt ggttaaaatc tgatggccgc actgattacg ttaaattatt cttccgatt    1380 gcgattcgtt tacgtgaaga taaaactaaa gctaatacat cgaagatgt atttggtgat    1440 tttcatgagg taactggtct aggttctggc agttcaggtc atcaccacca tcatcactaa    1500

<210> SEQ ID NO 22
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Ile Lys
        35                  40                  45

Lys Trp Pro Lys Pro Gly Ile Ala Thr Gln Ser Phe Gly Met Leu Thr
50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
130                 135                 140

Gly Ile Asn Lys Asn Ile Lys Phe Pro Ala Phe Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Ile Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
```

| | | | | |
|---|---|---|---|---|
| 385 | | 390 | 395 | 400 |

Ile Lys Val Asn Ala Gly Ser Gly Leu Lys Asp Lys Ala Gly Val Lys
                     405                            410                       415

Ser His Glu Leu Asp Arg Thr Arg Ile Met Glu Asn Gln Asn Tyr Tyr
                     420                            425                       430

Ile Gly Lys Ile Leu Glu Cys Glu Cys Asn Gly Trp Leu Lys Ser Asp
                     435                            440                       445

Gly Arg Thr Asp Tyr Val Lys Leu Phe Leu Pro Ile Ala Ile Arg Leu
      450                            455                            460

Arg Glu Asp Lys Thr Lys Ala Asn Thr Phe Glu Asp Val Phe Gly Asp
465                     470                            475                       480

Phe His Glu Val Thr Gly Leu Gly Ser Gly Ser Ser Gly His His His
                     485                            490                       495

His His His

<210> SEQ ID NO 23
<211> LENGTH: 1500
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 23

| | |
|---|---|
| atgattctta aaattctgaa cgaaatagca tctattggtt caactaaaca gaagcaagca | 60 |
| attcttgaaa agaataaaga taatgaattg cttaaacgag tatatcgtct gacttattct | 120 |
| cgtgggttac agtattatat caagaaatgg cctaaacctg gtattgctac ccagagtttt | 180 |
| ggaatgttga ctcttaccga tatgcttgac ttcattgaat tcacattagc tactcggaaa | 240 |
| ttgactggaa atgcagcaat tgaggaatta actggatata tcaccgatgg taaaaaagat | 300 |
| gatgttgaag ttttgcgtcg agtgatgatg cgagaccttg aatgtggtgc ttcagtatct | 360 |
| attgcaaaca agtttggcc aggtttaatt cctgaacaac ctcaaatgct cgcaagttct | 420 |
| tatgatgaaa aaggcattaa taagaatatc aaatttccag cctttgctca gttaaaagct | 480 |
| gatggagctc ggtgttttgc tgaagttaga ggtgatgaat tagatgatgt tcgtctttta | 540 |
| tcacgagctg gtaatgaata tctaggatta gatcttctta aggaagagtt aattaaaatg | 600 |
| accgctgaag cccgccagat tcatccagaa ggtgtgttga ttgatggcga attggtatac | 660 |
| catgagcaag ttaaaaagga gccagaaggc ctagattttc ttttttgatgc ttatcctgaa | 720 |
| aacagtaaag ctaagaatt cgccgaagta gctgaatcac gtactgcttc taatggaatc | 780 |
| gccaataaat ctttaaaggg aaccatttct gaaaagaag cacaatgcat gaagtttcag | 840 |
| gtctgggatt atgtcccgtt ggtagaaata tacagtcttc ctgcatttcg tttgaaatat | 900 |
| gatgtacgtt tttctaaact agaacaaatg acatctggat atgataaagt aattttaatt | 960 |
| gaaaaccagg tagtaaataa cctagatgaa gctaaggtaa tttataaaaa gtatattgac | 1020 |
| caaggtcttg aaggtattat tctcaaaaat atcgatggat tatgggaaaa tgctcgttca | 1080 |
| aaaaatcttt ataaatttaa agaagtaatt aaagttgatt taaaaattgt aggaatttat | 1140 |
| cctcaccgta aagaccctac taaagcgggt ggatttattc ttgagtcaga gtgtggaaaa | 1200 |
| attaaggtaa atgctggttc aggcttaaaa gataaagccg gtgtaaaatc gcatgaactt | 1260 |
| gaccgtactc gcattatgga aaaccaaaat tattatattg gaaaaattct agagtgcgaa | 1320 |
| tgcaacggtt ggttaaaatc tgatggccgc actgattacg ttaaattatt tcttccgatt | 1380 |

```
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 24
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
```

```
            340             345             350
Gly Leu Trp Glu Asn Ala Arg Ser Lys Asn Leu Tyr Lys Phe Lys Glu
            355                 360                 365

Val Ile Lys Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His
```

<210> SEQ ID NO 25
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac tcaaatgct cgcaagttct      420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc ttttgatgc ttatcctgaa      720
aacagtaaag ctaaagaatt cgccgaagta gctgaatcac gtactgcttc taatggaatc     780
gccaataaat cttaaaaggg aaccatttct gaaaagaag cacaatgcat gaagtttcag      840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt ttggttgatt taaaaattgt aggaatttat    1140
```

```
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 26
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
```

```
Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Leu Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
            485                 490                 495

His His His
```

<210> SEQ ID NO 27
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atgattctta aaattctgaa cgaaatagca tctattggtt caactaaaca gaagcaagca      60
attcttgaaa agaataaaga taatgaattg cttaaacgag tatatcgtct gacttattct    120
cgtgggttac agtattatat caagaaatgg cctaaacctg gtattgctac ccagagtttt    180
ggaatgttga ctcttaccga tatgcttgac ttcattgaat tcacattagc tactcggaaa    240
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca agtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc ttttttgatgc ttatcctgaa    720
aacagtaaag ctaagaattc gccgaagta gctgaatcac gtactgcttc taatggaatc    780
gccaataaat ctttaaaggg aaccatttct gaaaagaag cacaatgcat gaagtttcag    840
```

-continued

```
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt atggttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 28
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
```

```
        245                 250                 255
Ser Asn Gly Ile Ala Asn Lys Ser Leu Lys Gly Thr Ile Ser Glu Lys
        260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Met Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 29
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aagcattaa taagaatatc aaatttccag cctttgctca gttaaaagct     480
gatggagctc ggtgttttgc tgaagttaga ggtgatgaat tagatgatgt tcgtcttta     540 tcacgagctg gtaatgaata tctaggatta gatcttctta aggaagagtt aattaaaatg     600
```

```
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat ctttaaaggg aaccatttct gaaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt cgtgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 30  
<211> LENGTH: 499  
<212> TYPE: PRT  
<213> ORGANISM: Artificial Sequence  
<220> FEATURE:  
<223> OTHER INFORMATION: Description of Artificial Sequence: Synthetic  
    polypeptide

<400> SEQUENCE: 30

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
```

```
                195                 200                 205
Pro Glu Gly Val Leu Ile Asp Gly Glu Leu Val Tyr His Glu Gln Val
            210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Arg Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 31
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
```

```
gatgttgaag ttttgcgtcg agtgatgatg cgagaccttg aatgtggtgc ttcagtatct    360
attgcaaaca agtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc ttttttgatgc ttatcctgaa    720 aacagtaaag ctaaagaatt cgccgaagta gctgaatcac gtactgcttc taatggaatc    780
gccaataaat ctttaaaggg aaccatttct gaaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt actgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 32
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
```

```
                145                 150                 155                 160
        Asp Gly Ala Arg Cys Phe Ala Glu Val Arg Gly Asp Glu Leu Asp Asp
                        165                 170                 175

Val Arg Leu Leu Ser Arg Ala Gly Asn Glu Tyr Leu Gly Leu Asp Leu
                        180                 185                 190

Leu Lys Glu Glu Leu Ile Lys Met Thr Ala Glu Ala Arg Gln Ile His
                        195                 200                 205

Pro Glu Gly Val Leu Ile Asp Gly Glu Leu Val Tyr His Glu Gln Val
                        210                 215                 220

Lys Lys Glu Pro Glu Gly Leu Asp Phe Leu Phe Asp Ala Tyr Pro Glu
        225                 230                 235                 240

Asn Ser Lys Ala Lys Glu Phe Ala Glu Val Ala Glu Ser Arg Thr Ala
                        245                 250                 255

Ser Asn Gly Ile Ala Asn Lys Ser Leu Lys Gly Thr Ile Ser Glu Lys
                        260                 265                 270

Glu Ala Gln Cys Met Lys Phe Gln Val Trp Asp Tyr Val Pro Leu Val
                        275                 280                 285

Glu Ile Tyr Ser Leu Pro Ala Phe Arg Leu Lys Tyr Asp Val Arg Phe
                        290                 295                 300

Ser Lys Leu Glu Gln Met Thr Ser Gly Tyr Asp Lys Val Ile Leu Ile
        305                 310                 315                 320

Glu Asn Gln Val Val Asn Asn Leu Asp Glu Ala Lys Val Ile Tyr Lys
                        325                 330                 335

Lys Tyr Ile Asp Gln Gly Leu Glu Gly Ile Ile Leu Lys Asn Ile Asp
                        340                 345                 350

Gly Leu Trp Glu Asn Ala Arg Ser Lys Asn Leu Tyr Lys Phe Lys Glu
                        355                 360                 365

Val Ile Thr Val Asp Leu Lys Ile Val Gly Ile Tyr Pro His Arg Lys
                        370                 375                 380

Asp Pro Thr Lys Ala Gly Gly Phe Ile Leu Glu Ser Glu Cys Gly Lys
        385                 390                 395                 400

Ile Lys Val Asn Ala Gly Ser Gly Leu Lys Asp Lys Ala Gly Val Lys
                        405                 410                 415

Ser His Glu Leu Asp Arg Thr Arg Ile Met Glu Asn Gln Asn Tyr Tyr
                        420                 425                 430

Ile Gly Lys Ile Leu Glu Cys Glu Cys Asn Gly Trp Leu Lys Ser Asp
                        435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
        465                 470                 475                 480

Phe His Glu Val Thr Gly Leu Gly Ser Gly Ser Gly His His His
                        485                 490                 495

His His His

<210> SEQ ID NO 33
        <211> LENGTH: 1500
        <212> TYPE: DNA
        <213> ORGANISM: Artificial Sequence
        <220> FEATURE:
        <223> OTHER INFORMATION: Description of Artificial Sequence: Synthetic
              polynucleotide

<400> SEQUENCE: 33
atgattctta aaattctgaa cgaaatagca tctattggtt caactaaaca gaagcaagca      60
```

```
attcttgaaa agaataaaga taatgaattg cttaaacgag tatatcgtct gacttattct    120
cgtgggttac agtattatat caagaaatgg cctaaacctg gtattgctac ccagagtttt    180
ggaatgttga ctcttaccga tatgcttgac ttcattgaat tcacattagc tactcggaaa    240
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca aagtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat cttttaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt tacgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgcgaa   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 34
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp 100                 105                 110
Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Tyr Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 35
<211> LENGTH: 1500

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac tcaaatgct cgcaagttct      420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccgaaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat cttttaaggg aaccatttct gaaaagaag cacaatgcat gaagtttcag      840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta agacccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct aaaatgcgaa    1320
tgcaacggtt ggttaaaatc tgatggccgc actgattacg ttaaattatt tcttccgatt    1380
gcgattcgtt acgtgaaga taaaactaaa gctaatacat cgaagatgt atttggtgat      1440
tttcatgagg taactggtct aggttctggc agttcaggtc atcaccacca tcatcactaa    1500
```

<210> SEQ ID NO 36
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
```

```
            50                  55                  60
Leu Thr Asp Met Leu Asp Phe Ile Glu Phe Thr Leu Ala Thr Arg Lys
 65                  70                  75                  80

Leu Thr Gly Asn Ala Ala Ile Glu Glu Leu Thr Gly Tyr Ile Thr Asp
                     85                  90                  95

Gly Lys Lys Asp Asp Val Glu Val Leu Arg Arg Val Met Met Arg Asp
                    100                 105                 110

Leu Glu Cys Gly Ala Ser Val Ser Ile Ala Asn Lys Val Trp Pro Gly
                115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Lys Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480
```

```
Phe His Glu Val Thr Gly Leu Gly Ser Gly Ser Ser Gly His His His
            485                 490                 495

His His His

<210> SEQ ID NO 37
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaaagaatt cgccgaagta gctgaatcac gtactgcttc taatggaatc     780
gccaataaat ctttaaaggg aaccatttct gaaaagaag cacaatgcat gaagtttcag      840
gtctgggatt atgtcccgtt ggtagaaata tacagtcttc ctgcatttcg tttgaaatat     900
gatgtacgtt tttctaaact agaacaaatg acatctggat atgataaagt aatttttaatt    960 gaaaaccagg tagtaaataa cctagatgaa gctaaggtaa tttataaaaa gtatattgac    1020
caaggtcttg aagtattat tctcaaaaat atcgatggat tatgggaaaa tgctcgttca    1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg tgtaaaatc gcatgaactt    1260 gaccgtactc gcattatgga aaaccaaaat tattatattg gaaaaattct agagtgcgca    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500

<210> SEQ ID NO 38
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ile Leu Lys Ile Leu Asn Glu Ile Ala Ser Ile Gly Ser Thr Lys
```

-continued

```
1               5                   10                  15
Gln Lys Gln Ala Ile Leu Glu Lys Asn Lys Asp Asn Glu Leu Leu Lys
            20                  25                  30
Arg Val Tyr Arg Leu Thr Tyr Ser Arg Gly Leu Gln Tyr Tyr Ile Lys
            35                  40                  45
Lys Trp Pro Lys Pro Gly Ile Ala Thr Gln Ser Phe Gly Met Leu Thr
            50                  55                  60
Leu Thr Asp Met Leu Asp Phe Ile Glu Phe Thr Leu Ala Thr Arg Lys
 65                  70                  75                  80
Leu Thr Gly Asn Ala Ala Ile Glu Glu Leu Thr Gly Tyr Ile Thr Asp
            85                  90                  95
Gly Lys Lys Asp Asp Val Glu Val Leu Arg Arg Val Met Met Arg Asp
            100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Tyr Asp Glu Lys
            130                 135                 140
Gly Ile Asn Lys Asn Ile Lys Phe Pro Ala Phe Ala Gln Leu Lys Ala
145                 150                 155                 160
Asp Gly Ala Arg Cys Phe Ala Glu Val Arg Gly Asp Glu Leu Asp Asp
            165                 170                 175
Val Arg Leu Leu Ser Arg Ala Gly Asn Glu Tyr Leu Gly Leu Asp Leu
            180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
            210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
            245                 250                 255
Ser Asn Gly Ile Ala Asn Lys Ser Leu Lys Gly Thr Ile Ser Glu Lys
            260                 265                 270
Glu Ala Gln Cys Met Lys Phe Gln Val Trp Asp Tyr Val Pro Leu Val
            275                 280                 285
Glu Ile Tyr Ser Leu Pro Ala Phe Arg Leu Lys Tyr Asp Val Arg Phe
            290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
            325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
            370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
            405                 410                 415
Ser His Glu Leu Asp Arg Thr Arg Ile Met Glu Asn Gln Asn Tyr Tyr
            420                 425                 430
```

```
Ile Gly Lys Ile Leu Glu Cys Ala Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His
            485                 490                 495

His His His

<210> SEQ ID NO 39
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat agatgatgt tcgtctttta     540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aattttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg tgtaaaatc gcatgaactt    1260 gaccgtactc gcattatgga aaaccaaaat tattatattg gaaaaattct agagtgccat    1320
tgcaacggtt ggttaaaatc tgatggccgc actgattacg ttaaattatt tcttccgatt    1380
gcgattcgtt tacgtgaaga taaaactaaa gctaatacat cgaagatgt atttggtgat    1440 tttcatgagg taactggtct aggttctggc agttcaggtc atcaccacca tcatcactaa    1500

<210> SEQ ID NO 40
<211> LENGTH: 499
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

| | | | | | | | | | | | | | | | |
|---|---|---|---|---|---|---|---|---|---|---|---|---|---|---|---|
| Met | Ile | Leu | Lys | Ile | Leu | Asn | Glu | Ile | Ala | Ser | Ile | Gly | Ser | Thr | Lys |
| 1 | | | | 5 | | | | | 10 | | | | | 15 | |
| Gln | Lys | Gln | Ala | Ile | Leu | Glu | Lys | Asn | Lys | Asp | Asn | Glu | Leu | Leu | Lys |
| | | | 20 | | | | | 25 | | | | | 30 | | |
| Arg | Val | Tyr | Arg | Leu | Thr | Tyr | Ser | Arg | Gly | Leu | Gln | Tyr | Tyr | Ile | Lys |
| | | | 35 | | | | | 40 | | | | | 45 | | |
| Lys | Trp | Pro | Lys | Pro | Gly | Ile | Ala | Thr | Gln | Ser | Phe | Gly | Met | Leu | Thr |
| | 50 | | | | | 55 | | | | | 60 | | | | |
| Leu | Thr | Asp | Met | Leu | Asp | Phe | Ile | Glu | Phe | Thr | Leu | Ala | Thr | Arg | Lys |
| 65 | | | | | 70 | | | | | 75 | | | | | 80 |
| Leu | Thr | Gly | Asn | Ala | Ala | Ile | Glu | Glu | Leu | Thr | Gly | Tyr | Ile | Thr | Asp |
| | | | | 85 | | | | | 90 | | | | | 95 | |
| Gly | Lys | Lys | Asp | Asp | Val | Glu | Val | Leu | Arg | Arg | Val | Met | Met | Arg | Asp |
| | | | 100 | | | | | 105 | | | | | 110 | | |
| Leu | Glu | Cys | Gly | Ala | Ser | Val | Ser | Ile | Ala | Asn | Lys | Val | Trp | Pro | Gly |
| | | 115 | | | | | 120 | | | | | 125 | | | |
| Leu | Ile | Pro | Glu | Gln | Pro | Gln | Met | Leu | Ala | Ser | Ser | Tyr | Asp | Glu | Lys |
| | 130 | | | | | 135 | | | | | 140 | | | | |
| Gly | Ile | Asn | Lys | Asn | Ile | Lys | Phe | Pro | Ala | Phe | Ala | Gln | Leu | Lys | Ala |
| 145 | | | | | 150 | | | | | 155 | | | | | 160 |
| Asp | Gly | Ala | Arg | Cys | Phe | Ala | Glu | Val | Arg | Gly | Asp | Glu | Leu | Asp | Asp |
| | | | | 165 | | | | | 170 | | | | | 175 | |
| Val | Arg | Leu | Leu | Ser | Arg | Ala | Gly | Asn | Glu | Tyr | Leu | Gly | Leu | Asp | Leu |
| | | | 180 | | | | | 185 | | | | | 190 | | |
| Leu | Lys | Glu | Glu | Leu | Ile | Lys | Met | Thr | Ala | Glu | Ala | Arg | Gln | Ile | His |
| | | 195 | | | | | 200 | | | | | 205 | | | |
| Pro | Glu | Gly | Val | Leu | Ile | Asp | Gly | Glu | Leu | Val | Tyr | His | Glu | Gln | Val |
| | 210 | | | | | 215 | | | | | 220 | | | | |
| Lys | Lys | Glu | Pro | Glu | Gly | Leu | Asp | Phe | Leu | Phe | Asp | Ala | Tyr | Pro | Glu |
| 225 | | | | | 230 | | | | | 235 | | | | | 240 |
| Asn | Ser | Lys | Ala | Lys | Glu | Phe | Ala | Glu | Val | Ala | Glu | Ser | Arg | Thr | Ala |
| | | | | 245 | | | | | 250 | | | | | 255 | |
| Ser | Asn | Gly | Ile | Ala | Asn | Lys | Ser | Leu | Lys | Gly | Thr | Ile | Ser | Glu | Lys |
| | | | 260 | | | | | 265 | | | | | 270 | | |
| Glu | Ala | Gln | Cys | Met | Lys | Phe | Gln | Val | Trp | Asp | Tyr | Val | Pro | Leu | Val |
| | | 275 | | | | | 280 | | | | | 285 | | | |
| Glu | Ile | Tyr | Ser | Leu | Pro | Ala | Phe | Arg | Leu | Lys | Tyr | Asp | Val | Arg | Phe |
| | 290 | | | | | 295 | | | | | 300 | | | | |
| Ser | Lys | Leu | Glu | Gln | Met | Thr | Ser | Gly | Tyr | Asp | Lys | Val | Ile | Leu | Ile |
| 305 | | | | | 310 | | | | | 315 | | | | | 320 |
| Glu | Asn | Gln | Val | Val | Asn | Asn | Leu | Asp | Glu | Ala | Lys | Val | Ile | Tyr | Lys |
| | | | | 325 | | | | | 330 | | | | | 335 | |
| Lys | Tyr | Ile | Asp | Gln | Gly | Leu | Gly | Ile | Ile | Leu | Lys | Asn | Ile | Asp | |
| | | | 340 | | | | | 345 | | | | | 350 | | |
| Gly | Leu | Trp | Glu | Asn | Ala | Arg | Ser | Lys | Asn | Leu | Tyr | Lys | Phe | Lys | Glu |
| | | 355 | | | | | 360 | | | | | 365 | | | |
| Val | Ile | Asp | Val | Asp | Leu | Lys | Ile | Val | Gly | Ile | Tyr | Pro | His | Arg | Lys |
| | 370 | | | | | 375 | | | | | 380 | | | | |

```
Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
        420                 425                 430

Ile Gly Lys Ile Leu Glu Cys His Cys Asn Gly Trp Leu Lys Ser Asp
    435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His
```

<210> SEQ ID NO 41
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac ctcaaatgct cgcaagttct     420
tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
gccaataaat ctttaaaggg aaccatttct gaaaagaag cacaatgcat gaagtttcag     840
gtctgggatt atgtcccgtt ggtagaaata tacagtcttc ctgcatttcg tttgaaatat     900
gatgtacgtt tttctaaact agaacaaatg acatctggat atgataaagt aatttttaatt     960
gaaaaccagg tagtaaataa cctagatgaa gctaaggtaa tttataaaaa gtatattgac    1020
caaggtcttg aaggtattat tctcaaaaat atcgatggat tatgggaaaa tgctcgttca    1080
aaaaatcttt ataaatttaa agaagtaatt gatgttgatt taaaaattgt aggaatttat    1140
cctcaccgta agaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaccaaaat tattatattg gaaaaattct agagtgcaaa    1320
```

-continued

```
tgcaacggtt ggttaaaatc tgatggccgc actgattacg ttaaattatt tcttccgatt      1380
gcgattcgtt tacgtgaaga taaaactaaa gctaatacat tcgaagatgt atttggtgat      1440
tttcatgagg taactggtct aggttctggc agttcaggtc atcaccacca tcatcactaa      1500
```

<210> SEQ ID NO 42
<211> LENGTH: 499
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Gly Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335
```

```
Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Lys Cys Asn Gly Trp Leu Lys Ser Asp
                435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 43
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca aagtttggcc aggtttaatt cctgaacaac tcaaatgct cgcaagttct      420 tatgatgaaa aaggcattaa taagaatatc aaatttccag cctttgctca gttaaaagct     480
gatggagctc ggtgttttgc tgaagttaga ggtgatgaat tagatgatgt tcgtcttttta    540 tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc      780
gccaataaat ctttaaaggg aaccatttct gaaaagaag cacaatgcat gaagtttcag      840
gtctgggatt atgtcccgtt ggtagaaata tacagtcttc ctgcatttcg tttgaaatat     900
gatgtacgtt tttctaaact agaacaaatg acatctggat atgataaagt aattttaatt    960 gaaaccagg tagtaaataa cctagatgaa gctaaggtaa tttataaaaa gtatattgac     1020
caaggtcttg aaggtattat tctcaaaaat atcgatggat tatgggaaaa tgctcgttca    1080
```

-continued

```
aaaaatcttt ataaatttaa agaagtaatt gatgttgatt taaaaattgt aggaatttat    1140
cctcaccgta aagaccctac taaagcgggt ggatttattc ttgagtcaga gtgtggaaaa    1200
attaaggtaa atgctggttc aggcttaaaa gataaagccg gtgtaaaatc gcatgaactt    1260
gaccgtactc gcattatgga aaaccaaaat tattatattg gaaaaattct agagtgcaac    1320
tgcaacggtt ggttaaaatc tgatggccgc actgattacg ttaaattatt tcttccgatt    1380
gcgattcgtt tacgtgaaga taaaactaaa gctaatacat tcgaagatgt atttggtgat    1440
tttcatgagg taactggtct aggttctggc agttcaggtc atcaccacca tcatcactaa    1500
```

<210> SEQ ID NO 44
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285
```

```
Glu Ile Tyr Ser Leu Pro Ala Phe Arg Leu Lys Tyr Asp Val Arg Phe
    290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
            340                 345                 350
Gly Leu Trp Glu Asn Ala Arg Ser Lys Asn Leu Tyr Lys Phe Lys Glu
        355                 360                 365
Val Ile Asp Val Asp Leu Lys Ile Val Gly Ile Tyr Pro His Arg Lys
    370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
            420                 425                 430
Ile Gly Lys Ile Leu Glu Cys Asn Cys Asn Gly Trp Leu Lys Ser Asp
        435                 440                 445
Gly Arg Thr Asp Tyr Val Lys Leu Phe Leu Pro Ile Ala Ile Arg Leu
    450                 455                 460
Arg Glu Asp Lys Thr Lys Ala Asn Thr Phe Glu Asp Val Phe Gly Asp
465                 470                 475                 480
Phe His Glu Val Thr Gly Leu Gly Ser Gly Ser Gly His His His
                485                 490                 495

His His His

<210> SEQ ID NO 45
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac tcaaatgct cgcaagttct     420 tatgatgaaa aaggcattaa taagaatatc aaatttccag cctttgctca gttaaaagct     480
gatggagctc ggtgttttgc tgaagttaga ggtgatgaat tagatgatgt tcgtctttta     540
tcacgagctg gtaatgaata tctaggatta gatcttctta aggaagagtt aattaaaatg     600
accgctgaag cccgccagat tcatccagaa ggtgtgttga ttgatggcga attggtatac     660
catgagcaag ttaaaaagga gccagaaggc ctagattttc tttttgatgc ttatcctgaa     720
aacagtaaag ctaagaatt cgccgaagta gctgaatcac gtactgcttc taatggaatc     780
```

```
gccaataaat ctttaaaggg aaccatttct gaaaagaag cacaatgcat gaagtttcag   840
gtctgggatt atgtcccgtt ggtagaaata tacagtcttc ctgcatttcg tttgaaatat   900
gatgtacgtt tttctaaact agaacaaatg acatctggat atgataaagt aattttaatt   960
gaaaaccagg tagtaaataa cctagatgaa gctaaggtaa tttataaaaa gtatattgac  1020
caaggtcttg aaggtattat tctcaaaaat atcgatggat tatgggaaaa tgctcgttca  1080
aaaaatcttt ataaatttaa agaagtaatt gatgttgatt taaaaattgt aggaatttat  1140
cctcaccgta aagaccctac taaagcgggt ggatttattc ttgagtcaga gtgtggaaaa  1200
attaaggtaa atgctggttc aggcttaaaa gataaagccg gtgtaaaatc gcatgaactt  1260
gaccgtactc gcattatgga aaaccaaaat tattatattg gaaaaattct agagtgccgt  1320
tgcaacggtt ggttaaaatc tgatggccgc actgattacg ttaaattatt tcttccgatt  1380
gcgattcgtt tacgtgaaga taaaactaaa gctaatacat tcgaagatgt atttggtgat  1440
tttcatgagg taactggtct aggttctggc agttcaggtc atcaccacca tcatcactaa  1500
```

<210> SEQ ID NO 46
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

| Met | Ile | Leu | Lys | Ile | Leu | Asn | Glu | Ile | Ala | Ser | Ile | Gly | Ser | Thr | Lys |
|---|---|---|---|---|---|---|---|---|---|---|---|---|---|---|---|
| 1 | | | | 5 | | | | | 10 | | | | | 15 | |

| Gln | Lys | Gln | Ala | Ile | Leu | Glu | Lys | Asn | Lys | Asp | Asn | Glu | Leu | Leu | Lys |
|---|---|---|---|---|---|---|---|---|---|---|---|---|---|---|---|
| | | | 20 | | | | | 25 | | | | | 30 | | |

| Arg | Val | Tyr | Arg | Leu | Thr | Tyr | Ser | Arg | Gly | Leu | Gln | Tyr | Tyr | Ile | Lys |
|---|---|---|---|---|---|---|---|---|---|---|---|---|---|---|---|
| | | 35 | | | | | 40 | | | | | 45 | | | |

| Lys | Trp | Pro | Lys | Pro | Gly | Ile | Ala | Thr | Gln | Ser | Phe | Gly | Met | Leu | Thr |
|---|---|---|---|---|---|---|---|---|---|---|---|---|---|---|---|
| 50 | | | | | 55 | | | | | 60 | | | | | |

| Leu | Thr | Asp | Met | Leu | Asp | Phe | Ile | Glu | Phe | Thr | Leu | Ala | Thr | Arg | Lys |
|---|---|---|---|---|---|---|---|---|---|---|---|---|---|---|---|
| 65 | | | | | 70 | | | | | 75 | | | | | 80 |

| Leu | Thr | Gly | Asn | Ala | Ala | Ile | Glu | Glu | Leu | Thr | Gly | Tyr | Ile | Thr | Asp |
|---|---|---|---|---|---|---|---|---|---|---|---|---|---|---|---|
| | | | | 85 | | | | | 90 | | | | | 95 | |

| Gly | Lys | Lys | Asp | Asp | Val | Glu | Val | Leu | Arg | Arg | Val | Met | Met | Arg | Asp |
|---|---|---|---|---|---|---|---|---|---|---|---|---|---|---|---|
| | | | 100 | | | | | 105 | | | | | 110 | | |

| Leu | Glu | Cys | Gly | Ala | Ser | Val | Ser | Ile | Ala | Asn | Lys | Val | Trp | Pro | Gly |
|---|---|---|---|---|---|---|---|---|---|---|---|---|---|---|---|
| | | 115 | | | | | 120 | | | | | 125 | | | |

| Leu | Ile | Pro | Glu | Gln | Pro | Gln | Met | Leu | Ala | Ser | Ser | Tyr | Asp | Glu | Lys |
|---|---|---|---|---|---|---|---|---|---|---|---|---|---|---|---|
| 130 | | | | | 135 | | | | | 140 | | | | | |

| Gly | Ile | Asn | Lys | Asn | Ile | Lys | Phe | Pro | Ala | Phe | Ala | Gln | Leu | Lys | Ala |
|---|---|---|---|---|---|---|---|---|---|---|---|---|---|---|---|
| 145 | | | | | 150 | | | | | 155 | | | | | 160 |

| Asp | Gly | Ala | Arg | Cys | Phe | Ala | Glu | Val | Arg | Gly | Asp | Glu | Leu | Asp | Asp |
|---|---|---|---|---|---|---|---|---|---|---|---|---|---|---|---|
| | | | | 165 | | | | | 170 | | | | | 175 | |

| Val | Arg | Leu | Leu | Ser | Arg | Ala | Gly | Asn | Glu | Tyr | Leu | Gly | Leu | Asp | Leu |
|---|---|---|---|---|---|---|---|---|---|---|---|---|---|---|---|
| | | | 180 | | | | | 185 | | | | | 190 | | |

| Leu | Lys | Glu | Glu | Leu | Ile | Lys | Met | Thr | Ala | Glu | Ala | Arg | Gln | Ile | His |
|---|---|---|---|---|---|---|---|---|---|---|---|---|---|---|---|
| | | 195 | | | | | 200 | | | | | 205 | | | |

| Pro | Glu | Gly | Val | Leu | Ile | Asp | Gly | Glu | Leu | Val | Tyr | His | Glu | Gln | Val |
|---|---|---|---|---|---|---|---|---|---|---|---|---|---|---|---|
| 210 | | | | | 215 | | | | | 220 | | | | | |

| Lys | Lys | Glu | Pro | Glu | Gly | Leu | Asp | Phe | Leu | Phe | Asp | Ala | Tyr | Pro | Glu |
|---|---|---|---|---|---|---|---|---|---|---|---|---|---|---|---|
| 225 | | | | | 230 | | | | | 235 | | | | | 240 |

Asn Ser Lys Ala Lys Glu Phe Ala Glu Val Ala Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Arg Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Ser Gly His His His
                485                 490                 495

His His His

<210> SEQ ID NO 47
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atgattctta aaattctgaa cgaaatagca tctattggtt caactaaaca gaagcaagca       60
attcttgaaa agaataaaga taatgaattg cttaaacgag tatatcgtct gactattct      120 cgtgggttac agtattatat caagaaatgg cctaaacctg gtattgctac ccagagtttt     180
ggaatgttga ctcttaccga tatgcttgac ttcattgaat tcacattagc tactcggaaa     240
ttgactggaa atgcagcaat tgaggaatta actggatata tcaccgatgg taaaaaagat     300
gatgttgaag ttttgcgtcg agtgatgatg cgagaccttg aatgtggtgc ttcagtatct     360
attgcaaaca agtttggcc aggtttaatt cctgaacaac tcaaatgct cgcaagttct      420 tatgatgaaa aaggcattaa taagaatatc aaatttccag cctttgctca gttaaaagct     480
gatggagctc ggtgttttgc tgaagttaga ggtgatgaat tagatgatgt tcgtctttta    540

```
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc ttttgatgc ttatcctgaa    720 aacagtaaag ctaaagaatt cgccgaagta gctgaatcac gtactgcttc taatggaatc    780
gccaataaat ctttaaaggg aaccatttct gaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aattttaatt    960
gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt gatgttgatt taaaaattgt aggaatttat   1140
cctcaccgta agaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg gaaaaattct agagtgctct   1320
tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 48
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190
```

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Ser Cys Asn Gly Trp Leu Lys Ser Asp
                435                 440                 445

Gly Arg Thr Asp Tyr Val Lys Leu Phe Leu Pro Ile Ala Ile Arg Leu
450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 49
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgattctta aaattctgaa cgaaatagca tctattggtt caactaaaca gaagcaagca      60
attcttgaaa agaataaaga taatgaattg cttaaacgag tatatcgtct gacttattct     120
cgtgggttac agtattatat caagaaatgg cctaaacctg gtattgctac ccagagtttt     180
ggaatgttga ctcttaccga tatgcttgac ttcattgaat tcacattagc tactcggaaa     240

```
ttgactggaa atgcagcaat tgaggaatta actggatata tcaccgatgg taaaaaagat    300
gatgttgaag ttttgcgtcg agtgatgatg cgagaccttg aatgtggtgc ttcagtatct    360
attgcaaaca aagtttggcc aggtttaatt cctgaacaac ctcaaatgct cgcaagttct    420
tatgatgaaa aaggcattaa taagaatatc aaatttccag cctttgctca gttaaaagct    480
gatggagctc ggtgttttgc tgaagttaga ggtgatgaat tagatgatgt tcgtctttta    540
tcacgagctg gtaatgaata tctaggatta gatcttctta aggaagagtt aattaaaatg    600
accgctgaag cccgccagat tcatccagaa ggtgtgttga ttgatggcga attggtatac    660
catgagcaag ttaaaaagga gccagaaggc ctagattttc tttttgatgc ttatcctgaa    720
aacagtaaag ctaaagaatt cgccgaagta gctgaatcac gtactgcttc taatggaatc    780
gccaataaat ctttaaaggg aaccatttct gaaaaagaag cacaatgcat gaagtttcag    840
gtctgggatt atgtcccgtt ggtagaaata tacagtcttc ctgcatttcg tttgaaatat    900
gatgtacgtt tttctaaact agaacaaatg acatctggat atgataaagt aatttttaatt   960 gaaaaccagg tagtaaataa cctagatgaa gctaaggtaa tttataaaaa gtatattgac   1020
caaggtcttg aaggtattat tctcaaaaat atcgatggat tatgggaaaa tgctcgttca   1080
aaaaatcttt ataaatttaa agaagtaatt gatgttgatt taaaaattgt aggaatttat   1140
cctcaccgta aagaccctac taaagcgggt ggatttattc ttgagtcaga gtgtggaaaa   1200
attaaggtaa atgctggttc aggcttaaaa gataaagccg gtgtaaaatc gcatgaactt   1260
gaccgtactc gcattatgga aaaccaaaat tattatattg aaaaattct agagtgctgg    1320 tgcaacggtt ggttaaaatc tgatggccgc actgattacg ttaaattatt tcttccgatt   1380
gcgattcgtt tacgtgaaga taaaactaaa gctaatacat tcgaagatgt atttggtgat   1440
tttcatgagg taactggtct aggttctggc agttcaggtc atcaccacca tcatcactaa   1500
```

<210> SEQ ID NO 50
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140
```

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
            165                 170                 175

Val Arg Leu Leu Ser Arg Ala Gly Asn Glu Tyr Leu Gly Leu Asp Leu
        180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Trp Cys Asn Gly Trp Leu Lys Ser Asp
        435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His

<210> SEQ ID NO 51
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
atgattctta aaattctgaa cgaaatagca tctattggtt caactaaaca gaagcaagca    60
attcttgaaa agaataaaga taatgaattg cttaaacgag tatatcgtct gacttattct   120
cgtgggttac agtattatat caagaaatgg cctaaacctg gtattgctac ccagagtttt   180
ggaatgttga ctcttaccga tatgcttgac ttcattgaat tcacattagc tactcggaaa   240
ttgactggaa atgcagcaat tgaggaatta actggatata tcaccgatgg taaaaaagat   300
gatgttgaag ttttgcgtcg agtgatgatg cgagaccttg aatgtggtgc ttcagtatct   360
attgcaaaca aagtttggcc aggtttaatt cctgaacaac tcaaatgctc gcaagttct   420
tatgatgaaa aaggcattaa taagaatatc aaatttccag cctttgctca gttaaaagct   480
gatggagctc ggtgttttgc tgaagttaga ggtgatgaat agatgatgt tcgtctttta   540
tcacgagctg gtaatgaata tctaggatta gatcttctta aggaagagtt aattaaaatg   600
accgctgaag cccgccagat tcatccagaa ggtgtgttga ttgatggcga attggtatac   660
catgagcaag ttaaaaagga gccagaaggc ctagattttc tttttgatgc ttatcctgaa   720
aacagtaaag ctaaagaatt cgccgaagta gctgaatcac gtactgcttc taatggaatc   780
gccaataaat ctttaaaggg aaccatttct gaaaaagaag cacaatgcat gaagtttcag   840
gtctgggatt atgtcccgtt ggtagaaata tacagtcttc ctgcatttcg tttgaaatat   900
gatgtacgtt tttctaaact agaacaaatg acatctggat atgataaagt aatttaatt   960
gaaaaccagg tagtaaataa cctagatgaa gctaaggtaa tttataaaaa gtatattgac  1020
caaggtcttg aaggtattat tctcaaaaat atcgatggat tatgggaaaa tgctcgttca  1080
aaaaatcttt ataaatttaa agaagtaatt gatgttgatt taaaaattgt aggaatttat  1140
cctcaccgta aagaccctac taaagcgggt ggatttattc ttgagtcaga gtgtggaaaa  1200
attaaggtaa atgctggttc aggcttaaaa gataaagccg gtgtaaaatc gcatgaactt  1260
gaccgtactc gcattatgga aaaccaaaat tattatattg gaaaaattct agagtgcgaa  1320
tgcaacggtt ggttaaaatc tcgtggccgc actgattacg ttaaattatt tcttccgatt  1380
gcgattcgtt acgtgaaga taaaactaaa gctaatacat cgaagatgt atttggtgat  1440
tttcatgagg taactggtct aggttctggc agttcaggtc atcaccacca tcatcactaa  1500
```

<210> SEQ ID NO 52
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

```
Gly Lys Lys Asp Asp Val Glu Val Leu Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
            210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Arg
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu Gly Ser Gly Ser Gly His His His
                485                 490                 495

His His His
```

```
<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Leu Gly Ser Gly Ser Ser Gly
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5
```